United States Patent
Veen et al.

(10) Patent No.: US 9,603,542 B2
(45) Date of Patent: Mar. 28, 2017

(54) ELECTRO-PHYSIOLOGICAL MEASUREMENT WITH REDUCED MOTION ARTIFACTS

(75) Inventors: Jeroen Veen, Eindhoven (NL); Mohammed Meftah, Eindhoven (NL); Nicolaas Lambert, Eindhoven (NL); Bart Michiel De Boer, Eindhoven (NL); Bastiaan Feddes, Eindhoven (NL); Lena Gourmelon, Eindhoven (NL); Ronald Rietman, Eindhoven (NL); Sri Andari Husen, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 987 days.

(21) Appl. No.: 13/383,302

(22) PCT Filed: Jul. 6, 2010

(86) PCT No.: PCT/IB2010/053089
§ 371 (c)(1),
(2), (4) Date: Jan. 10, 2012

(87) PCT Pub. No.: WO2011/007292
PCT Pub. Date: Jan. 20, 2011

(65) Prior Publication Data
US 2012/0116198 A1    May 10, 2012

(30) Foreign Application Priority Data

Jul. 13, 2009 (EP) ..................... 09165307

(51) Int. Cl.
*A61B 5/04* (2006.01)
*A61B 5/0428* (2006.01)
*A61B 5/00* (2006.01)

(52) U.S. Cl.
CPC ........ *A61B 5/04284* (2013.01); *A61B 5/7214* (2013.01); *A61B 2562/0209* (2013.01); *A61B 2562/046* (2013.01)

(58) Field of Classification Search
CPC ... A61B 5/7203; A61B 5/7207; A61B 5/7214; A61B 5/04004; A61B 5/0428; A61B 2562/0214
(Continued)

(56) References Cited

U.S. PATENT DOCUMENTS

| 3,744,482 A | 7/1973 | Kaufman et al. |
| 4,147,981 A | 4/1979 | Williams |

(Continued)

FOREIGN PATENT DOCUMENTS

| DE | 4324374 | 12/1993 |
| DE | 4324374 A1 | 12/1993 |

(Continued)

OTHER PUBLICATIONS

Kim et al. "Common Mode Noise Cancellation for Electrically Non-Contact ECG Measurement System on a Chair" IEEE Engineering in Medicine and Biology Society, Conference Proceedings p. 5881-5883 (Feb. 2005).*

*Primary Examiner* — Lee S Cohen
*Assistant Examiner* — Erin M Cardinal

(57) ABSTRACT

An apparatus and method (4,5,6,7,2) for capacitive measurement of electrophysiological signals (1) suppresses or reduces motion artifacts by providing a feedback mechanism. An average voltage between a capacitive sensor electrode (1) and the body (3) is controlled so as to reduce or minimize motion-induced signals.

10 Claims, 16 Drawing Sheets

(58) Field of Classification Search
USPC .................. 600/372, 382, 509, 544–545
See application file for complete search history.

(56) References Cited

U.S. PATENT DOCUMENTS

| | | | |
|---|---|---|---|
| 4,248,244 A | 2/1981 | Charnitski et al. | |
| 6,807,438 B1 | 10/2004 | Brun Del Re et al. | |
| 6,960,945 B1* | 11/2005 | Bonin | 327/111 |
| 7,088,175 B2* | 8/2006 | Krupka | 330/69 |
| 2002/0038092 A1 | 3/2002 | Stanaland et al. | |
| 2002/0198469 A1* | 12/2002 | Bridger et al. | 600/586 |
| 2004/0073104 A1* | 4/2004 | Brun del Re et al. | 600/372 |
| 2004/0254435 A1 | 12/2004 | Mathews et al. | |
| 2005/0154270 A1 | 7/2005 | Nuccitelli et al. | |
| 2006/0122478 A1 | 6/2006 | Sliepen et al. | |
| 2007/0135701 A1* | 6/2007 | Fridman et al. | 600/382 |
| 2008/0079435 A1 | 4/2008 | Williams et al. | |
| 2008/0139953 A1* | 6/2008 | Baker et al. | 600/509 |
| 2009/0079606 A1* | 3/2009 | Terry et al. | 341/143 |

FOREIGN PATENT DOCUMENTS

| | | |
|---|---|---|
| DE | 10021714 | 2/2001 |
| DE | 10021714 A1 | 2/2001 |
| DE | 102004039291 | 3/2006 |
| DE | 102004039291 A1 | 3/2006 |
| JP | 2007082938 A | 4/2007 |
| WO | 2006066566 A2 | 6/2006 |
| WO | 2008135952 A1 | 11/2008 |
| WO | 2008152588 A2 | 12/2008 |

* cited by examiner

ELECTRO-PHYSIOLOGICAL MEASUREMENT WITH REDUCED MOTION ARTIFACTS

FIELD OF THE INVENTION

The present invention generally relates to devices, methods, and programs for electro-physiological measurements.

BACKGROUND OF THE INVENTION

Conventional electrodes for measuring electrophysiological signals like EEG, EMG and ECG may be attached to the skin of the patient by means of an adhesive. Generally, a gel may be used to ensure a good galvanic contact between the electrode and the body. The adhesive and the gel can cause skin irritation and are uncomfortable for continuous monitoring.

An alternative to such electrodes are capacitive sensors where the capacitive coupling between the skin and an electrode is used to measure surface potentials. Such capacitive sensors are disclosed in US 2011/0248729 which describes a sensor system and method for the capacitive measurement of electromagnetic signals having a biological origin. Capacitive sensors for electro-physiological measurements suffer from motion artifacts due to the time-varying distance between capacitive electrode and the body or skin. In many applications such motion artifacts may present problems.

SUMMARY OF THE INVENTION

It is an object of the present invention to provide an apparatus comprising a capacitive sensor, and a respective method, with reduced motion artifacts.

In accordance with an aspect of the present invention an apparatus is presented which is configured to measure at least one electrophysiological signal of a body and comprises at least one capacitive sensor electrode as well as an arrangement configured to control an average voltage between the at least one capacitive sensor electrode and the body for reducing or minimizing motion-induced signals. Precise signal measurement is thus achieved even in case of movements of the body to be measured.

At least one reference electrode may be provided which is arranged close to or in galvanic contact with the body. The reference electrode enables setting or detecting a reference potential for increasing measurement precision.

The at least one reference electrode may be connected to a voltage source, a current source or a reference potential allowing to define the potential or electric conditions of the reference electrode and thus of the body.

In accordance with one or more of the embodiments a voltage or current source may be coupled to at least one of the sensor electrode and an input of a buffer amplifier connected to the sensor electrode enabling a defined setting of the measurement conditions of the sensor electrode.

In accordance with one or more of the embodiments, at least two sensor electrodes may be coupled to inputs of a differential amplifier to the at least one reference electrode. A precise differential measurement is thus possible.

The apparatus may comprise at least two or three sensor electrodes configured to measure essentially the same electrophysiological signal and being arranged at different distances to the body and/or supplied with different average voltages. Due to this arrangement, a reliable feedback signal can be generated based on the output signals of the sensor electrodes so as to bring the average voltages to a defined value. The defined value can have a certain preset value or may optionally be zero. The motion-induced signal can thus be reduced or eliminated.

In accordance with one or more of the embodiments at least one buffer amplifier is provided which is configured to convert an output signal of the sensor electrode applied to an input of the buffer amplifier into an output signal while keeping the average voltage on the sensor electrode at a level defined by a signal applied to a further input of the buffer amplifier. This concept allows minimization of motion-induced signals.

At least three sensor electrodes may be arranged in a triangular fashion or in form of concentric circles so as to ensure co-location and gaining of reliable information on motion-induced signals.

In accordance with one or more of the embodiments, at least three sensor electrodes may be provided wherein one of the sensor electrodes may be arranged in the center of the sensor electrode arrangement and the other sensor electrodes may surround the center electrode in form of segments being arranged in form of a ring or a matrix. This arrangement enables detection and/or elimination of motion-induced signals.

In another embodiment, the apparatus comprises at least three sensor electrodes arranged in the form of small segments, the segments of all electrodes being distributed in an interspersed manner. Such an arrangement enables detection and/or elimination of motion-induced signals.

In accordance with another aspect of the invention, or according to one or more of the embodiments the or an apparatus may comprise an oscillator or vibrator for oscillating or vibrating at least one of the sensor electrode, the reference electrode or a support or casing supporting or housing the sensor electrode or reference electrode. The induced motion of the electrode allows detection and compensation of motion-induced signals and thus increases measurement precision regarding the electrophysiological signals to be measured. The apparatus may in accordance with one or more of the embodiments further comprise a feedback loop coupled to the oscillator or vibrator to generate a feedback signal for reducing or minimizing the average voltage.

The frequency of the oscillation or vibration may be set outside of the bioelectric frequency band of the electrophysiological signal to be measured so as to allow clear distinction between these signals.

A synchronous detector may be provided which issues a detection signal to the arrangement and thus contributes to signal measurement precision.

In accordance with one or more of the embodiments an extractor may be configured to extract, from the sensor electrode signal, an indicator of an average voltage between the at least one sensor electrode and the body, wherein the apparatus is configured to use the indicator to control a compensation signal. This structure allows an efficient compensation and thus minimization of motion artifacts.

According to another aspect of the invention, or in accordance with one or more of the embodiments an apparatus may comprise an estimator configured to determine a sensor signal power estimate or an sensor signal entropy estimate of at least one output signal of the at least one sensor electrode and to generate a feedback signal based on the at least one output signals of the at least one sensor electrodes so as to bring the average voltages to a defined value.

In any one of the above embodiments or according to other embodiments, the apparatus may be configured to provide an adaptive power minimization. This power minimization provides an indication and reduction of motion-induced power.

According to one or more embodiments an or the apparatus may comprise means configured for at least one or more, in any arbitrary combination, of the following:

using an iterative optimization algorithm to adapt the compensation signal $\hat{V}_{AV}(t_1)$ in order to achieve minimization of the sensor signal power P (t), updating the compensation signal $\hat{V}_{AV}(t_1)$, as given by $$\hat{V}_{AV}(t_1) = \hat{V}_{AV}(t_0) - \alpha \frac{\partial P(t)}{\partial \hat{V}_{AV}(t)}\bigg|_{t=t_0}$$

wherein an adaptation constant $\alpha$ is provided for controlling the convergence speed and the steady-state noise, obtaining an estimate of a gradient by finite difference approximation:

$$\frac{\partial P(t)}{\partial \hat{V}_{AV}(t)}\bigg|_{t=t_1} = \frac{P(t_1) - P(t_0)}{\hat{V}_{AV}(t_1) - \hat{V}_{AV}(t_0)},$$

using modulation or wobbling to determine the local gradient, prefiltering the sensor signal and using only a certain frequency band for determining the power, using an adaptive Shannon entropy minimization, determining the information entropy by a probability mass function p (x) of the signal, i.e.

$$H(X) = -E\{\log x\} = -\sum_{x \in \chi} p(x)\log p(x)$$

obtaining H(X) from a probability mass function estimate $\hat{p}(x)$ $$\hat{H}(X) = -\sum_{i=1}^{n} \hat{p}(x_i)\log \hat{p}(x_i).$$

obtaining $$\hat{V}_{AV}(t_1) = \hat{V}_{AV}(t_0) - \alpha \frac{\partial \hat{H}(X,t)}{\partial \hat{V}_{AV}(t)}\bigg|_{t=t_0}.$$

In any one of the above embodiments, or according to another aspect of the invention, or other embodiments independent from the above or below embodiments, an equalizer may be provided for equalizing a transfer function $V_o/V_{bio}$, wherein $V_o$ is an output signal of a buffer amplifier configured to receive an electrophysiological signal $V_{bio}$ of interest, the apparatus configured to adaptively control the transfer $V_o/V_{bio}$, such that equalization is achieved. This approach provides good signal measurement.

In any one of the above embodiments or according to another aspect of the invention, or in other embodiments independent from the above or below embodiments, a method may comprise at least one of, or an or the apparatus may comprise means configured for at least one of:

applying a reference signal $V_{ref}$ to the body using at least one reference electrode for the purpose of equalizing the buffer input capacitance of capacitive biosignal sensing, modulating the reference signal to a value above the maximum frequency that is expected in the signal of interest, subtracting the applied reference signal from the measured and buffered reference signal, demodulating and low pass filtering the resulting signal and using this signal to control the amplification. An effective suppression of motion-induced signals is thus provided.

In any one of the above embodiments or in other embodiments, a feedback arrangement may comprise an integrator in the feedback arrangement so as to bring the gain of the buffer amplifier to unity. Motion components can thus be suppressed with reliable circuitry.

In any one of the above embodiments or in other embodiments, a digital circuit may be provided for implementing the equalization scheme or other of the above functions in the digital domain, providing high efficiency and good flexibility.

According to another aspect of the invention, or in any one of the above embodiments or in other embodiments independent from the above or below embodiments, a method may comprise at least one of, or an or the apparatus may comprise a controller for controlling the average voltage between the body and electrode to minimize the motion-induced signal, reconstructing the input signal using a measured variation of a capacitance of the sensor electrode, and deriving a compensation signal by processing the reconstructed signal.

In accordance with a further aspect of the invention, a method for measuring at least one electrophysiological signal of a body is provided which comprises the feature of controlling an average voltage between a capacitive sensor electrode and the body so as to reduce or minimize motion-induced signals.

In accordance with another aspect of the invention, a computer program may comprise program code means for causing a computer to carry out steps of controlling an average voltage between a capacitive sensor electrode and the body so as to reduce or minimize motion-induced signals.

It shall be understood that one or more embodiments of the invention can also be any combination of any one or more of the above features or of any one or more of the dependent claims with the respective independent claim.

At least one or more of the embodiments of the invention are based on the insight that the motion induced signals are proportional to the electric field between the skin and the electrode and the motion components along that electric field.

One or more embodiments propose feedback mechanisms that control the average voltage between capacitive electrode and body such that the motion-induced signals are reduced or minimized.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Generally, contactless (capacitive) measurement of electrophysiological signals is able to overcome disadvantages of skin irritation during prolonged usage, restriction of the patient from free moving and providing less comfort for the patient, i.e. the patient is aware of being monitored.

In the technique according to one or more embodiments described in the following, a capacitor is effectively formed in which the human tissue acts as one of the capacitor plates and the plate electrode of the sensor acts as the other capacitor plate. In the capacitive sensing, no galvanic contact to the skin is needed (i.e. contactless sensing), thereby not needing skin preparation and a sticky patch with conductive gel for establishing a good electrical contact. It is apparently advantageous, in particular, when a lengthy measurement has to be conducted.

Figure 1:
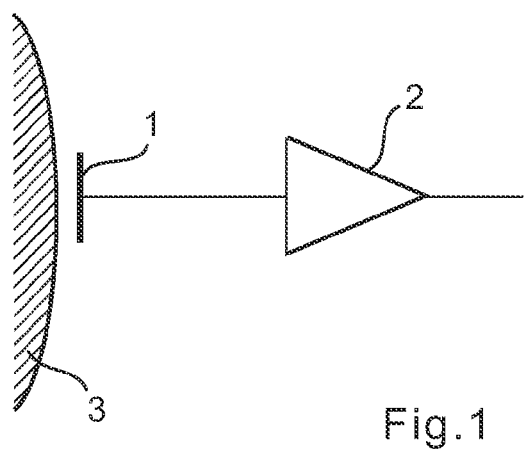
FIG. 1 shows a basic diagram illustrating a measurement arrangement.

FIG. 1 shows a basic drawing of a circuit diagram of a capacitive sensor electrode 1 with a buffer amplifier 2. The sensor is arranged close to or in contact with the body or skin 3 of a patient, and comprises a parallel plate capacitor connected to the high impedance buffer amplifier 2. The buffer 2 connected to the measurement electrode is able to convert the impedance level from high-ohmic to low-ohmic, such that it can be transported across a cable to the measurement system without being affected by interference.

In the diagram of FIG. 1, the equation $$\frac{V_{ac}}{V_{dc}} = \frac{d_{ac}}{d_{dc}} \qquad (1)$$

applies where $V_{dc}$ is the average potential difference between the capacitor electrodes 1, 3, $V_{ac}$ is the motion-induced voltage variation detected by the buffer amplifier 2, $d_{dc}$ is the average distance between the capacitor electrodes 1, 3, $d_{ac}$ is the motion-induced time distance variation between the capacitor electrodes 1, 3.

For a more complex geometry the behavior is slightly modified but essentially the same.

The actually measured ac signal $V_{measured}$ on the electrode 1 is an addition of the motion-induced signal $V_{ac}$ and the desired bio signal $V_{bio}$ on the skin 3. It is not easy to separate these signals without further information on desired signal or motion:

$$V_{measured} = V_{ac} + V_{bio}. \qquad (2)$$

Basically, in an electric field between two parallel capacitor plates at different potentials, motion-induced distance variation between the plates causes unwanted signals proportional to the electric field and the distance variation.

When the two parallel capacitor plates are held at equal average potential, the electric field (due to external sources) is now mostly external of the plates. The sense electrode can be shielded from these external influences by proper shielding or active guarding. Evidently, external electric fields, e.g. from the mains, can be shielded by well-known proper shielding techniques like grounded shielding and active guards. But the electric field between skin 3 and electrode 1 is an essential part of the desired signal coupling and cannot be shielded. In accordance with one or more of the embodiments, the electric field is controlled, for example by controlling the average voltage between electrode and skin and/or by avoiding any insulating materials or electrically floating conductors that could introduce uncontrollable charges in the space where motion occurs.

Electro-potential differences between skin and electrode may also stem from material differences between the two surfaces. These potential differences are related to the work function differences in vacuum, to galvanic cell potentials in an electrolyte environment, and to the tribo-electric series for rubbed electrodes in air. The potential differences depend on the material and surface conditions and are typically in the order of a volt for the work function and electrolyte potentials. For surfaces in air very similar potential differences exist and they can vary by several tenths of a volt with temperature, humidity, contamination, oxidation. In the case of the human skin the surface potential also depends on many physiological aspects, e.g. sodium- and potassium-ion densities in the skin depend on hydratation and stretching. Therefore, even when body and sense electrode are at the same galvanic potential, a significant electric field between skin and electrode can still be present which, combined with distance electrode-to-body variation, will cause motion-induced signals.

In accordance with one or more of the embodiments a mechanism or features are provided that control the average voltage between body and electrode such that it minimizes the induced motion signal. The methods and devices according to embodiments described below effectively minimize the electric field between body and electrode and thus remove a root cause of the motion artifacts.

To control the average voltage between body 3 and electrode 1, a reference electrode 4 is provided that is in galvanic contact with the body 3. The control can be achieved in various ways, see for example the circuit diagrams of FIGS. 2 to 11.

Figure 2:
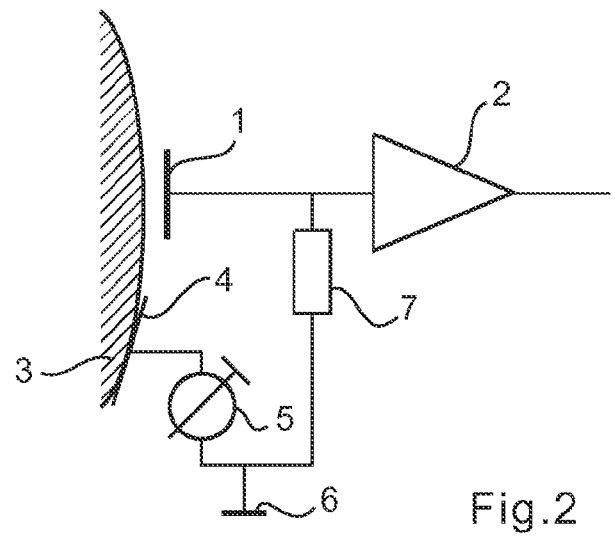
FIG. 2 shows schematically and exemplarily a representation of an embodiment in accordance with the invention.

FIG. 2 shows an embodiment wherein the voltage of the reference electrode 4 is controlled by a voltage source 5 connected to the reference electrode 4. In this embodiment, the voltage source 5 is connected between the reference electrode 4 and ground or reference potential 6. A resistor 7 is connected between the reference potential 6 and the buffer 2.

Figure 3:
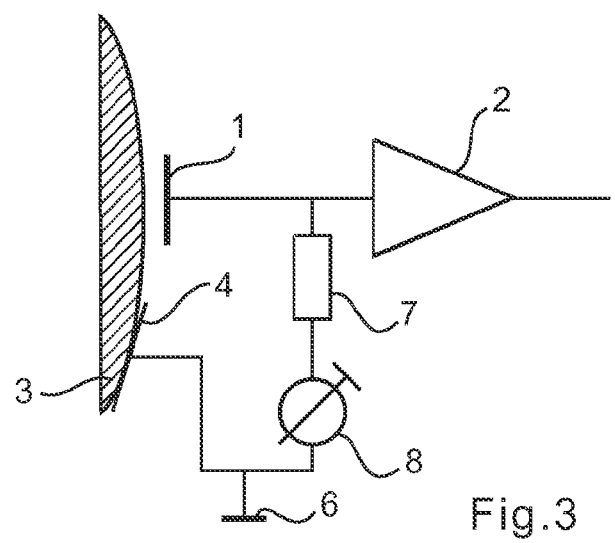
FIG. 3 illustrates schematically and exemplarily a representation of a further embodiment in accordance with the invention.
Figure 4:
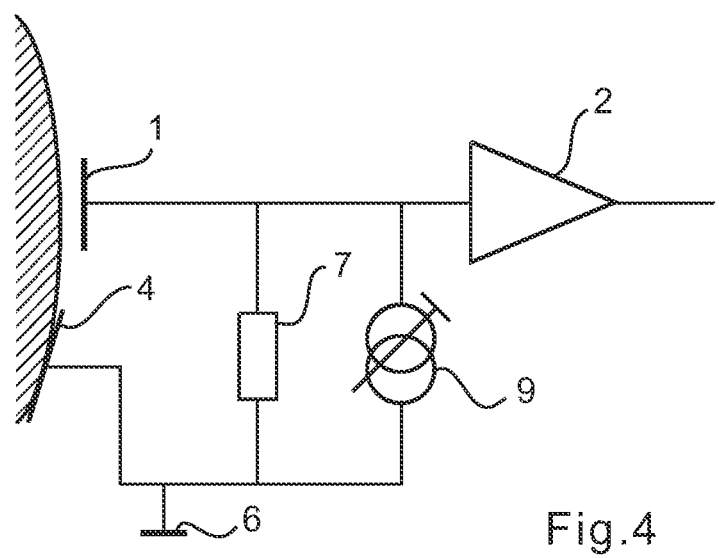
FIGS. 4 to 11 show further embodiments in accordance with the invention.

FIGS. 3, 4 show embodiment wherein the voltage of the sense electrode 1 is controlled through a voltage source or a current source. In FIG. 3, a voltage source 8 is connected to the sense electrode 1 via the resistor 7. In this embodiment, the reference electrode 4 is directly connected to the ground or reference potential 6. The voltage source 8 is connected between a terminal of the resistor 7 and the ground or reference potential 6. The other terminal of the resistor 7 is connected to and the buffer 2 and the sense electrode 1.

In FIG. 4, a current source 9 is connected between the output of the sense electrode 1 and the ground or reference potential 6. In this embodiment, the resistor 7 is connected in parallel to the current source 9. The reference electrode 4 is directly connected to the ground or reference potential 6. In this embodiment, the output of the sense electrode 1 is commonly connected to a terminal of the resistor 7, the input of the buffer amplifier 2 and a terminal of the current source 9. The other terminal of the resistor 7 is connected to the ground or reference potential 6.

When the input impedance of the buffer amplifier 2 and the parallel resistor 7 are extremely high, for example more than 10 Gigaohm or more than 50 Gigaohm, the current source solution of e.g. FIG. 4 can effectively behave like an integrating control circuit.

In other embodiments any technique can be used that is able to measure the induced motion signal for controlling the voltage between the body 3 and sense electrode 1 in a minimizing feedback mechanism. Some examples are as follows. When the motion is not known, post-processing filtering techniques can be applied to the sense electrode signal such that (all or a part of) the natural motion-induced signal (that is for example outside the frequency band of the desired signal) is separated from the sense electrode signal and this separated signal is used for feedback in a minimizing scheme. This may involve some stepwise or modulated feedback signal to find out the proper direction towards minimization. This is further explained in a below described embodiment.

When the motion is known by other means, e.g. from an actuator-induced known motion system, or from a separate motion sensor like an accelerometer or an optical sensor or so, this known motion can be correlated/multiplied with the signal from the sense electrode 1 to obtain a proper feedback signal. Because the average correlation/multiplication result is signed it can be used directly as a feedback signal without the need of additional modulation. Examples are provided in below described embodiments.

The feedback circuit itself can act on the measurement electrode 1 or on the body reference electrode 4, and the circuit ground 6 can be chosen at the body reference potential or close to the electrode potential or somewhere else.

In these or other embodiments the average voltage between body 3 and electrode 1 is controlled.

The feedback loop can be relatively slow because the average voltage between body and electrode for which the motion artifacts are minimized varies only slowly due to temperature drift and electro-chemical surface changes. For the optimal average voltage between body and electrode the motion-induced signals are minimized for a wide range of frequencies. Also note that the feedback loop can automatically compensate for various other slowly varying offsets in the system.

In order to control the average voltage between body and electrode, a galvanic connection between the feedback system and both body and electrode is needed. But because the feedback is relatively slow and only leakage currents have to be overcome, the requirements on that galvanic connection are very mild. For example even a reference electrode 4 that touches the body 3 only indirectly through a slightly conductive medium is sufficient. An extreme but practical case is a relatively large electrode 4 that has a clear capacitive link to the body 3 and only a very poorly conductive contact, e.g. through a layer of textile. The poorly conductive contact is enough for the relatively slow feedback and for avoiding clipping. The capacitive part of the reference electrode 4 can now induce motion artifacts in the same manner as described above. But if multiple capacitive sensors are connected to that same reference electrode and we only measure voltage differences between those multiple capacitive sensors, the motion-induced signal of the reference electrode 4 is a common mode signal. That common mode signal is easily removed by a differential or instrumentation amplifier when the influence of further parasitics in the capacitive sensors is properly avoided.

Figure 5:
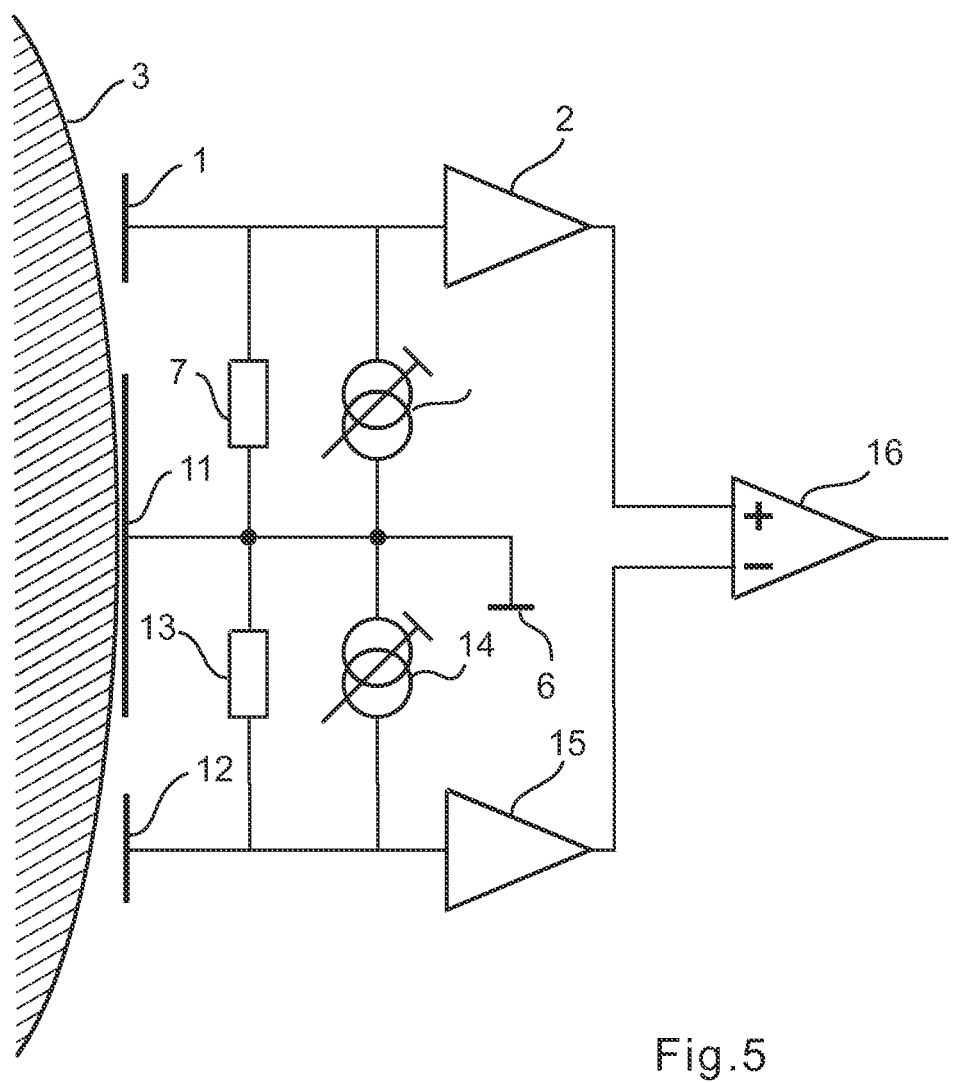
Figure 6:
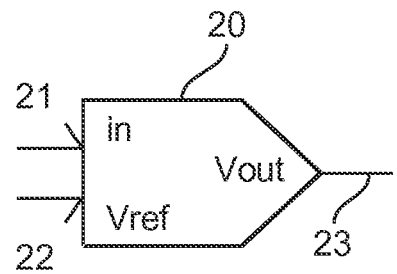

FIG. 5 illustrates an embodiment where motion artifacts from a large common capacitive reference electrode 11 can be eliminated by a differential or instrumentation amplifier 16. Only a very slight galvanic conduction between reference electrode 11 and skin 3 is needed to prevent clipping. The embodiment of FIG. 5 comprises the components of FIG. 4 connected as described above, and additionally includes a second sense electrode 12, and a current source 14 connected between the output of the sense electrode 12 and the ground or reference potential 6. In this embodiment, a resistor 13 is connected in parallel to the current source 14. The reference electrode 11 is directly connected to the ground or reference potential 6, and to terminals of the resistors 7, 13, and of the current sources 9, 14. In this embodiment, the output of the sense electrode 12 is commonly connected to a terminal of the resistor 13, the input of a buffer amplifier 15 and a terminal of the current source 14. The other terminal of the resistor 13 is connected to the ground or reference potential 6. The output of buffer 2 is connected to the non-inverting input of the differential amplifier 16 whereas the output of buffer 15 is connected to the inverting input of the differential amplifier 16. The connection between the outputs of the buffers 2, 15 and the inputs of amplifier 16 can also be inverted or provided by means of interconnecting elements.

Because one or more embodiments of the invention use a relatively slow feedback they can be combined with many other techniques that attempt to improve signal quality and remove artifacts. E.g. standard motion artifacts filtering techniques can be combined with embodiments of the invention because they work in different ways.

Embodiments of the method may be implemented so that any motion-induced variation in transfer function of the desired electro-physiological signals is, or is not, compensated for. E.g. a neutralization can be used to reduce these types of motion artifacts and can be combined with embodiments of the invention.

An advantage of the above or below described embodiments or more generally an electric circuit added to the biological signal amplifier(s), for reducing common-mode interference, such as a driven-right-leg system, is that unwanted common mode signals between two or more measurement electrodes such as electrodes 1, 12 may be reduced. Practical implementations may typically also set the average voltage between body 3 and electrodes. The advantages of such a driven-right-leg system and of the described embodiments can be easily combined because the feedback of one or more embodiments according to the invention may be relatively slow while the unwanted common mode signals are at much higher frequencies like the 50 Hz or 60 Hz power grid frequency.

In the following, embodiments of a capacitive sensor with reduced motion artifacts using multiple co-located electrodes will be described.

As mentioned above, capacitive sensors for electro-physiological measurements may suffer from motion artifacts due to varying distance between the capacitive electrode(s) and the body. These artifacts may to a large extent be due to the presence of an average electric field between skin and electrode. In accordance with one or more of the embodiments described below or above, it is proposed to combine measured signals from multiple co-located electrodes to control the average voltage between capacitive electrode and body such that the motion-induced signals are reduced or minimized.

By combining signals from multiple co-located electrodes information can be gained on the motion-induced signals. Two, three or more electrodes may be used. A particular choice of a three-electrode solution is described in more detail below. The embodiments provide some details on the associated measurement circuits and electrodes.

In the embodiments described below, circuit elements are provided that comply with requirements of extremely low input capacitance, extremely high input impedance, low offset, and control over average electrode voltage. Further, an example of an analog circuit for suitable signal combination is provided.

In addition some electrode geometries are shown that are able to meet symmetry requirements in accordance with one or more of the embodiments.

As mentioned above, in the basic circuit diagram of a capacitive sensor electrode 1 with buffer amplifier 2 shown in FIG. 1, the equation $$\frac{V_{ac}}{V_{dc}} = \frac{d_{ac}}{d_{dc}} \tag{3}$$

applies.

The quantities $V_{dc}$, $d_{dc}$ and $d_{ac}$ that underlie the motion-induced signal $V_{ac}$ are essentially unknown in a practical situation.

The actually measured ac signal $V_{measured}$ on the electrode is an addition of the motion-induced signal $V_{ac}$ and the desired bio signal $V_{bio}$ on the skin that is not easily separated without further information on desired signal or motion:

$$V_{measured} = V_{ac} + V_{bio}. \tag{4}$$

When combining, in accordance with one or more of the embodiments, multiple electrodes that measure the potential of the skin at essentially the same location so they share essentially the same $V_{bio}$, but at different average voltages and/or different average distance, information about the motion can be obtained and a suitable feedback signal may be provided for obtaining a signal with reduced motion artifacts.

In accordance with one or more of the embodiments a three electrode solution is provided. This variant of the above concept will be discussed in more detail. Three co-located electrodes a, b and c are used which sense essentially the same (unknown) bio signal $V_{bio}$ and undergo essentially the same (unknown) motion $d_{ac}$. Electrode a is at (unknown) average distance d, and (unknown) average voltage V. Electrode b is at average distance d+Δd and at average voltage V+ΔV, and electrode c is also at average distance d+Δd but at average voltage V−ΔV. The static geometric parameter Δd and the static voltage difference ΔV are known. Applying the equations for induced motion signals we arrive at the following measured signals on the three electrodes:

$$V_a = V_{bio} + V d_{ac}/d \tag{5}$$

$$V_b = V_{bio} + (V + \Delta V) d_{ac}/(d + \Delta d) \tag{6}$$

$$V_c = V_{bio} + (V - \Delta V) d_{ac}/(d + \Delta d). \tag{7}$$

By combining these measured signals the unknown $V_{bio}$ and $d_{ac}$ can be eliminated and a useful relation between the unknown V and d can be set up, e.g.

$$V = d(\Delta V/\Delta d)(V_b + V_c - 2V_a)/(V_b - V_c). \tag{8}$$

The distance d between electrode a and skin is not known, but obviously it has to be positive.

Therefore the signal combination $$(V_b + V_c - 2V_a)/(V_b - V_c) \tag{9}$$

is proportional to the unknown V, and even though the proportionality factor is unknown, the sign of the proportionality factor is known. So this expression can be used in a feedback scheme to drive the unknown V towards zero. This essentially makes the electric field for electrode a zero, which in turn makes the measured signal on electrode equal to $V_{bio}$ hence motion-artifact free. Other functions of the measured signals are also possible.

To illuminate the relation between the three signals further we first consider the situation where the circuits are perfectly balanced around optimum average voltage V=0. In this case the measured signal $V_a$ on electrode a represents the desired bio signal $V_{bio}$ directly, and the measured signals $V_b$ and $V_c$ on electrodes b and c deviate symmetrically around it by a voltage difference of +/−ΔV $d_{ac}/(d+\Delta d)$. In other words the voltage differences $V_b - V_a$ and $V_a - V_c$ are equal. If now the average voltage on all three electrodes rises such that V>0, the voltage difference between electrode b and a becomes $$V_b - V_a = d_{ac}(d\Delta V - V\Delta d)/d(d + \Delta d) \tag{10}$$

while the voltage difference between electrode a and c becomes $$V_a - V_c = d_{ac}(d\Delta V + V\Delta d)/d(d + \Delta d). \tag{11}$$

Clearly, the signals on electrodes b and c are no longer symmetric around electrode a and this effect can be exploited to generate a feedback signal that drives the unknown average voltage V to zero.

Apart from the function mentioned above, there are many other possibilities for feedback. E.g. when Δd>0 and ΔV>0, the following function can be used:

$$\exp(V_b - V_a) - \exp(V_a - V_c) = \exp(d_{ac}\Delta V/(d+\Delta d))\sinh(-d_{ac}V\Delta d/d(d+\Delta d)).$$

If treating the expression as a function of the quickly varying motion $d_{ac}$, we see that the sin h ( ) function in the expression is anti-symmetric around zero and has a slope proportional to −V, while the exponential function is always positive with a positive slope. So the average of this function is a non-zero value with sign opposite to the unknown V that can be used to drive the system towards the desired situation with V=0. Many other non-linear functions like $\log(V_b-V_a)-\log(V_a-V_c)$ or $(V_b-V_a)^2-(V_a-V_c)^2$ lead to similar results.

Usually, there is non-zero (but unknown) motion $d_{ac}$. When there is no motion no motion artifacts occur. The proposed three electrode solution provides sufficient symmetry between the three electrodes and measurements: offset and gain of the three measurements systems is sufficiently equal, the effect of parasitics on the measurements low, and the variables $\Delta V$, $V$, $V_{bio}$, d, $\Delta d$ and $d_{ac}$ as defined above have sufficiently equal values for all three electrodes. This can all be achieved by proper electronic and geometric design. Some of the electronic aspects and geometrical aspects of the design are discussed below. Variations of the three electrode solution described above are possible. Adding more electrodes can provide more information and more accurate feedback.

An embodiment using only two electrodes can be used to improve other mechanisms that provide feedback for optimising the average voltage for minimum motion artifacts. Two co-located electrodes that are at the same distance but at different average voltage combined with a separate motion estimating mechanism can be used to drive the average voltage in the right direction towards the optimum. Two co-located electrodes that are at the same average voltage but at different distance can help separating the motion artefact signal from the bio signal.

Some schematics will be described below. For each sense electrode a circuit 20 (FIG. 6) is provided that translates the capacitively sensed electrode signal as faithful as possible into a signal, and also allows control of the average voltage on the electrode. This functionality is symbolised in FIG. 6 by symbol 20 illustrating an electrode buffer amplifier that faithfully translates the capacitive signal on the electrode connected to an "in" port 21 to an output signal Vout at an output 23, while keeping the average voltage on the electrode at a level given by input 22, Vref.

Figure 7:
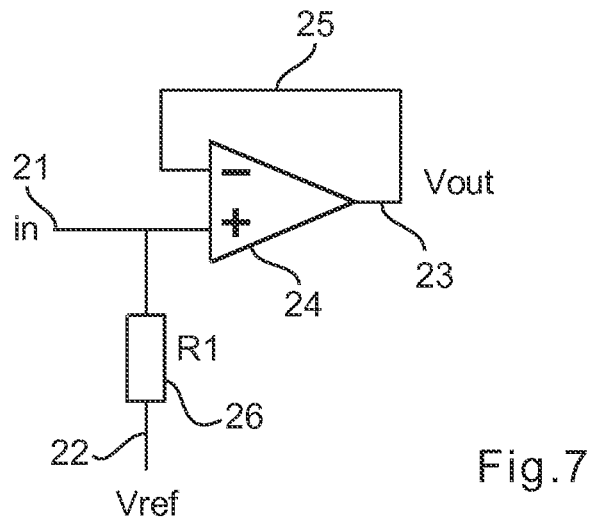

A basic implementation of this functionality using a standard ultra-high input impedance operational amplifier 24 is shown in FIG. 7. The embodiment of FIG. 7 provides a simple implementation of the electrode buffer amplifier using a very high input impedance buffer amplifier 24 with unity gain. The reference voltage is supplied from input 22 via a resistor 26 to the non-inverting input of amplifier 24 which is also connected to the input 21. The output 23 of the amplifier 24 is directly fed back via feedback loop 25 to the inverting input of the amplifier so as to provide unity gain.

This circuit of FIG. 7 provides a trade-off between desirable high R1 value of resistor 26 for high input impedance with little bio signal filtering and an undesirable offset due to amplifier input bias current.

Figure 8:
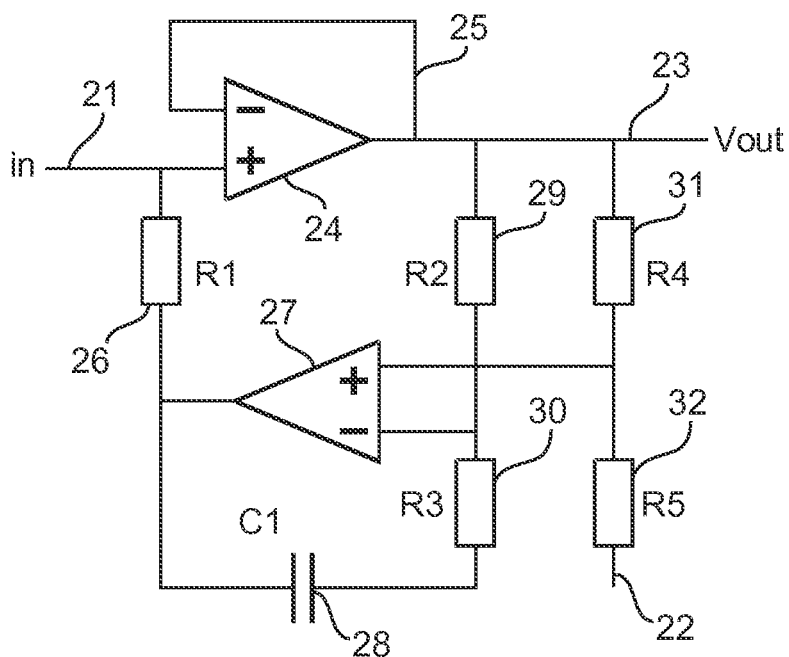

FIG. 8 shows an embodiment which largely overcomes this trade-off by the addition of an additional integrator circuit 27, 28 that reduces or removes the offset of the input stage (leaving only integrator's input voltage offset) and provides a mechanism to boost the level of the input impedance of the circuit even higher. The operational amplifier 27 comprises a capacitor 28 and a resistor 30 in its feedback loop so as to function as an integrator. The output 23 is connected to a voltage divider comprising the resistor 30 connected in series with a resistor 29, the connecting point being connected to the inverting input of amplifier 27. The output 23 is further connected to a second voltage divider comprising resistors 31, 32 connected in series between the output 23 and the input 22, Vref, the connecting point being connected to the non-inverting input of amplifier 27.

The time-constant R2*C1 (components 29, 28) drives the slow integration of the offset compensation, resistor 30, R3, provides a means to improve phase stability at higher frequencies, and the ratio of the sum of resistors to the resistor 31 (R5+R4)/R4 serves as a multiplying factor for the effective input impedance of the circuit.

In practice these circuit can have a significant input capacitance which together with varying skin-electrode capacitance due to motion may create undesirable motion artifacts in signal transfer function of the circuit. As already mentioned above this can be reduced by known active guarding and neutralisation circuits.

Figure 9:
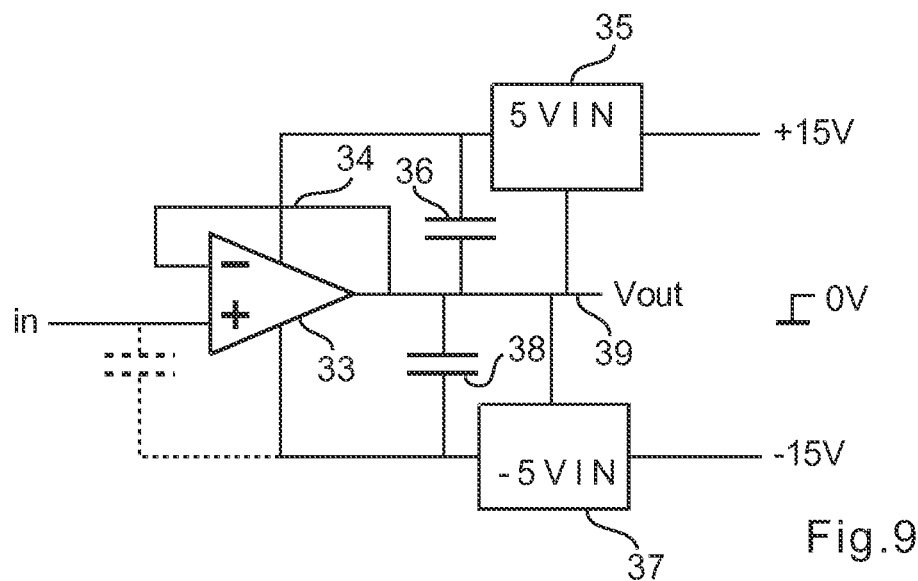

FIG. 9 shows an embodiment in form of an example circuit with strongly reduced input capacitance due to actively coupled amplifier supply rails. FIG. 9 shows a possibility to effectively eliminate the input capacitance by actively coupling the amplifier's internal power supply rails to the unity-gain output. This technique may optionally be combined with known active guarding against external parasitic capacitances (not shown here). The circuit shown in FIG. 9 uses a unity gain amplifier 33 having a negative feedback loop 34 directly connecting the amplifier output to the inverting input of amplifier 33. The circuit comprises a standard power regulator 35, providing positive supply voltage of e.g. +5 V from a +15 V rail, and a standard power regulator 37, providing negative supply voltage of e.g. −5 V from a −15 V rail. The +5 V, −5 V voltage outputs of the regulators 35, 37 are connected and referenced to the output 39 of the amplifier 33 by means of capacitors 36, 38, resp. The circuit as shown uses standard power regulators but other circuits employing the same basic thought are also possible, e.g. using charge pumps or a floating power supply like a battery or a transformer. In this and other embodiments any parasitic capacitance is either actively shielded or actively coupled to the unity-gain output.

Figure 10:
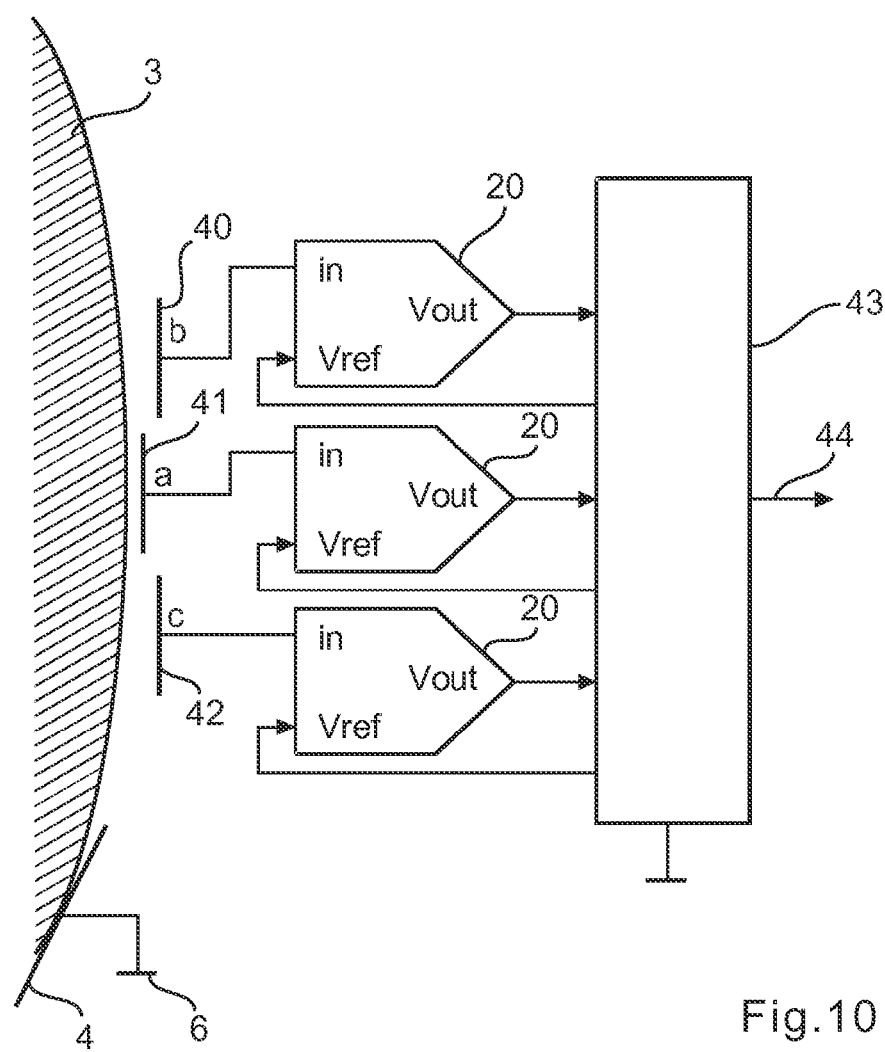

FIG. 10 shows a diagram that illustrates a basic implementation of an embodiment implementing a 3-electrode solution. Electrodes b and c, corresponding to electrodes 40, 42 are slight further away from the skin than electrode a, (electrode 41). A filter block 43 receives the signals from electrodes a, b and c via a circuit 20 such as shown in, and described with reference to, FIG. 6, generates proper feedback signals for the average voltage of each electrode 40 to 42, and generates an output signal 44 with strongly reduced motion artifacts.

The filter block 43 and the three buffer amplifiers 20 can be implemented in many ways, including digital circuits.

Figure 11:
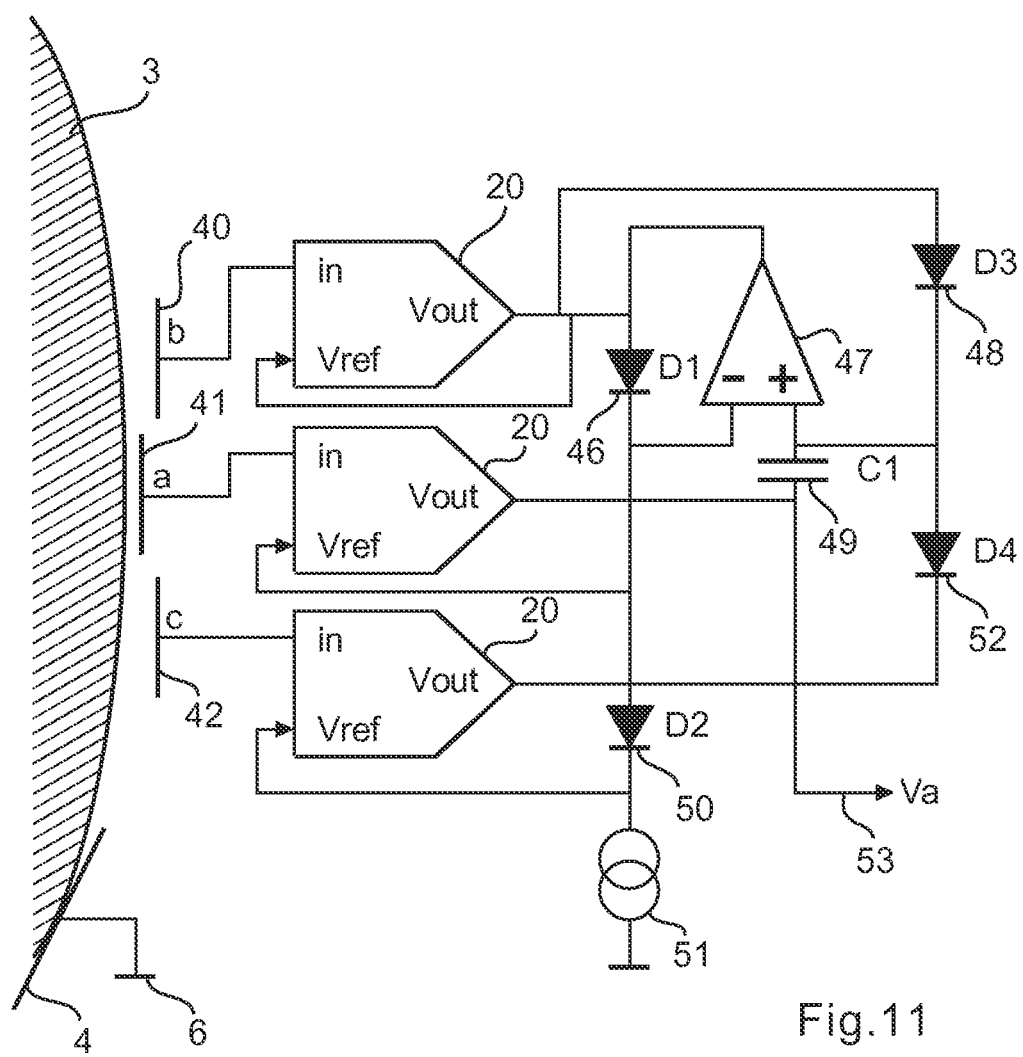

FIG. 11 shows an embodiment incorporating a possible analog filter implementation for the 3-electrode solution. FIG. 11 shows a simplified analog implementation of the suggested 3-electrode solution. Here a current source 51, diodes 46 (D1) and 50 (D2) and an operational amplifier 47 provide the +$\Delta V$ and −$\Delta V$ reference voltages, applied to the Vref inputs of the circuits 20, for the electrodes 40 to 42, and diodes 48 (D3) and 52 (D4) together with capacitor C1 derive a suitable non-linear feedback function from the measured electrode signals. The effective motion-filtering time-constant of the non-linear feedback circuit is proportional to capacitance 49 (C1) divided by the current supplied by the current source 51. A terminal of the capacitance 49 is connected to the non-inverting input of amplifier 47, cathode of diode 48, and anode of diode 52. The other terminal of the capacitance 49 is connected to the output of circuit 20 coupled with electrode 41, and the output 53. The diodes 46, 50 are coupled in series between the output of amplifier 47 and the current source 51. The anode of diode 46 is connected to the Vref input of circuit 20 coupled with electrode 40. The cathode of diode 46 is connected to the Vref input of circuit 20 coupled with electrode 41, and the cathode of diode 50 is connected to the Vref input of circuit 20 coupled with electrode 42.

Regarding the embodiments using co-located electrodes as described above and below, optional features of the suggested approach is that the electrodes 40 to 42 measure essentially the same bio signal $V_{bio}$, share essentially the same electro-potential difference V between skin surface and electrode surface, share essentially the same motion $d_{ac}$, and that electrodes b and c are at essentially the same common distance from the skin. A first measure to take is to put the electrodes 40 to 42 closely together and provide a suitable mechanical attachment for positioning them at the skin surface, see e.g. FIG. 12.

Figure 12:
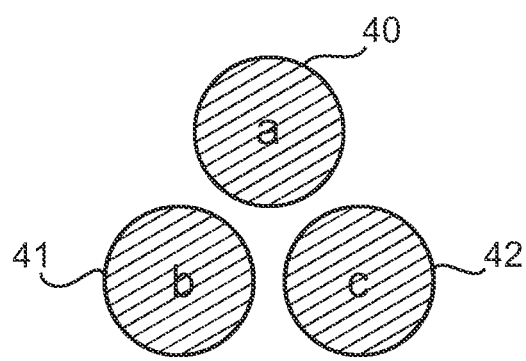
FIGS. 12 to 17 illustrate further embodiments of electrode arrangements in accordance with the invention.

FIG. 12 shows electrodes 40 to 42 (a, b and c) closely co-located so they experience the same signals and motion, e.g. arranged in form of a triplet or triangle.

Figure 13:
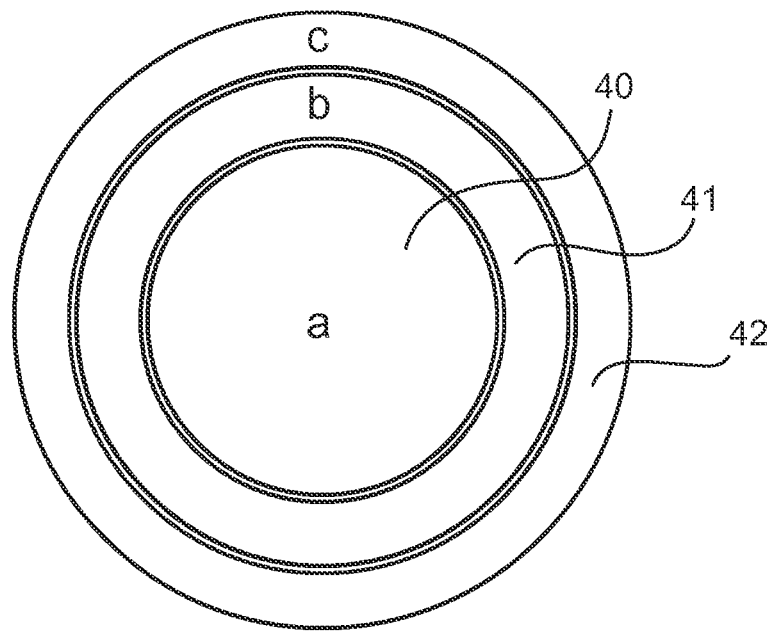
Figure 14:
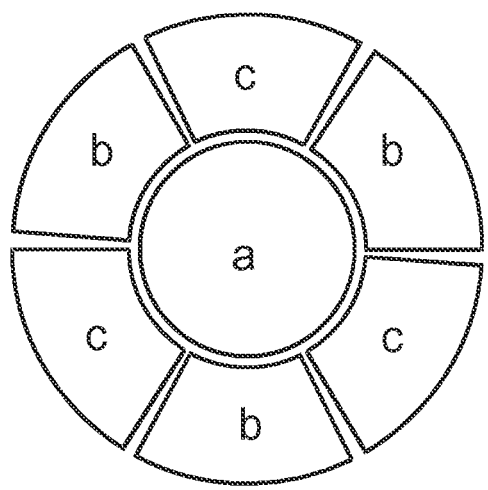
Figure 15:
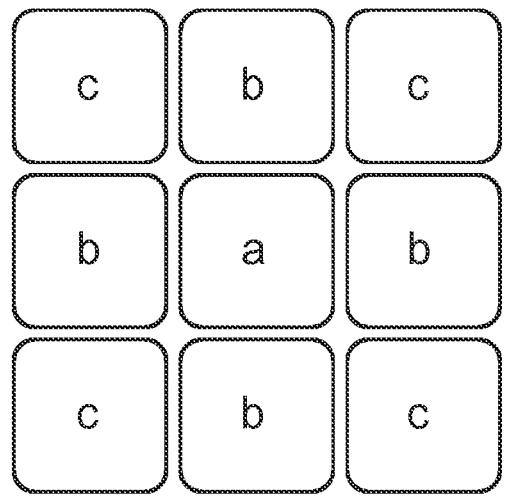

To be less sensitive to skin curvature, electrode tilt and signal gradients along the skin surface, it may be beneficial to use a more symmetric electrode assembly, see e.g. FIGS. 13, 14, 15. In the embodiments of FIGS. 14, 15, each of the electrodes b and c are split up into multiple electrode segments. In the embodiment of FIG. 14, the segments of electrodes c, b are alternatingly arranged along a circle surrounding the center electrode a. These multiple segments of an electrode can be electrically connected to a single buffer amplifier for that electrode. The embodiment of FIG. 14 provides a more symmetric electrode assembly that also conserves capacitive symmetry between electrode b and c. The various segments of electrode b are electrically connected. Same holds for electrode c.

In the embodiment of FIG. 15, the electrode segments of electrodes b, c are matrix-like arranged around the center electrode a and show a four-fold symmetry.

Figure 16:
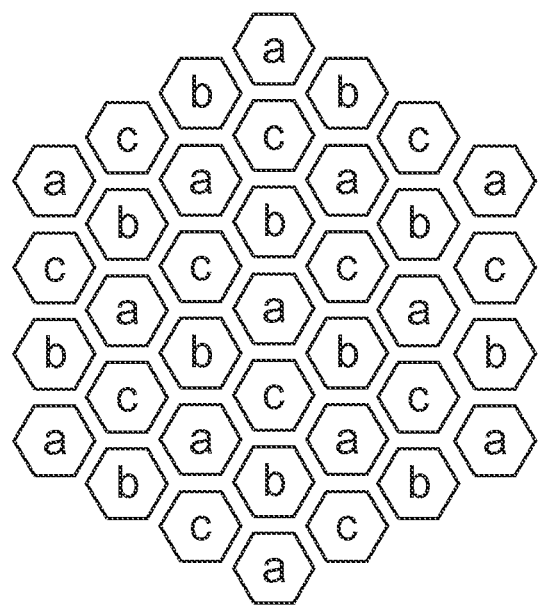
Figure 17:
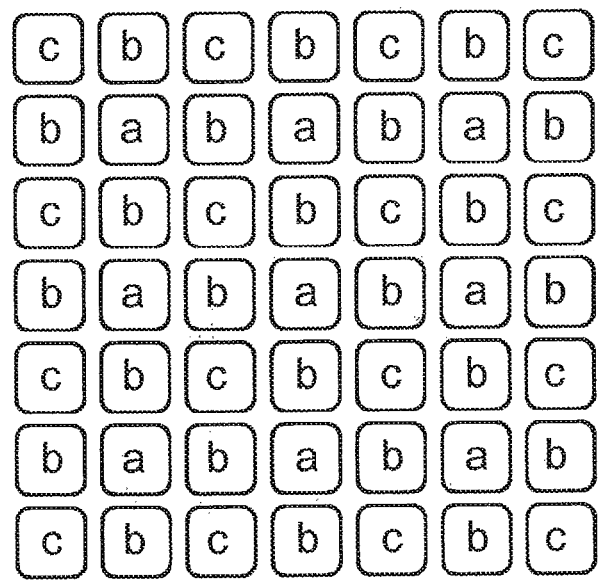

For proper performance of the electronic circuitry a certain minimum electro surface area is required. To make the co-location of the electrodes even better it is possible to split up the area into multiple smaller electrode segments, see a FIG. 16 and FIG. 17. This provides even better averaging over small deviations in distance to skin and signal gradients. Both embodiments of FIGS. 16, 17 provide averaging over many smaller electrodes. The letters in the segments illustrate the electrode to which the respective segments pertains. FIG. 16 shows a honeycomb-like structure and FIG. 17 a matrix-like arrangement wherein the electrode segments are arranged in an interleaved manner.

Obviously more geometries are possible with similar advantages. For other solutions with a different number of co-located electrodes than three, similar reasoning leads to slightly different electrode patterns.

Note that the inter-electrode capacitance can be significant and tends to grow when using multiple electrode segments. For avoiding or reducing such an effect, the electrodes can be shielded from each other using a suitable active guarding scheme (not shown here). External fields may also be properly guarded such that the electrodes are only exposed to the intended skin area.

In accordance with one or more of the embodiments according to the invention, which may be implemented alone or may be freely combined with one or more of the above described embodiments, a motion artifacts reduction in capacitive bioelectric sensing is achieved using a vibrating probe.

As mentioned above, the combination of skin-electrode distance variation and the presence of an offset voltage (i.e. electric field) across the skin-electrode capacitive coupling, e.g. due to electro-chemical potential differences and amplifier bias offset, may cause artifacts in electrophysiological measurements. In the embodiments according to the invention, described below, a method and device are proposed that significantly reduce the artifacts by compensating the offset voltage using a vibrating capacitive probe in combination with a feedback mechanism.

In the embodiments described above, the motion induced signals may be proportional to both the electric field between electrode and skin and to the motion components along that electric field. As mentioned above, the average voltage between the body and electrode may be actively controlled such that the electric field between body and electrode and thus the motion-induced signal are minimized. To control the average voltage between body and electrode, a reference electrode is provided. Since only small and slowly time-varying voltages have to be controlled, the requirements on that galvanic connection are very mild. For example even a reference electrode that touches the body only indirectly through a slightly conductive medium is sufficient. The control can be achieved in various ways, see the circuit diagrams in the attached illustrating FIGS. 2 to 4 for some examples illustrating different configurations for controlling the electrode-body voltage drop. The following description explains a solution of how to make the capacitive coupling between body and electrode field free.

Figure 18:
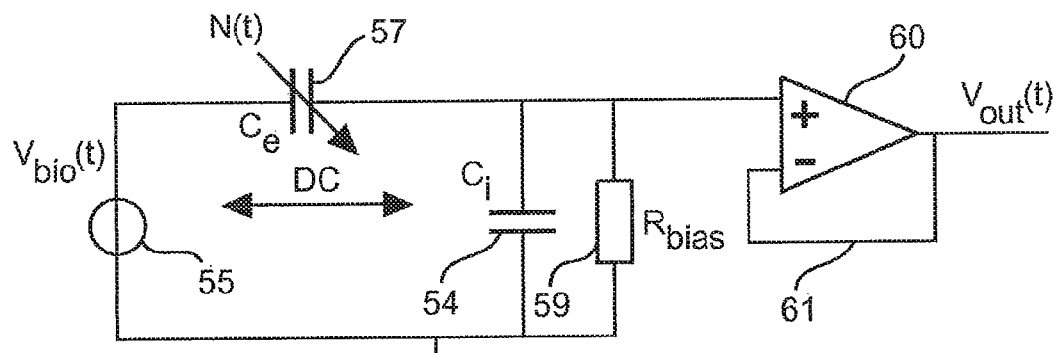
FIG. 18 shows exemplarily another embodiment in accordance with the invention, FIGS. 19 and 20 exemplify aspects of the embodiments of FIG. 18.

As mentioned above, the combination of skin-electrode distance variation and the presence of an offset voltage (i.e. electric field) across the skin-electrode capacitive coupling, e.g. due to electro-chemical potential differences and amplifier bias offset, may cause artifacts in electrophysiological measurements. A detailed description of the problem will be given by means of FIG. 18 showing a schematic drawing of a capacitive electrophysiological measurement. From left to right the drawing shows a bioelectric signal 55, $V_{bio}(t)$, the skin-electrode capacitance 57, $C_e$, which is time-varying according to N(t), an input capacitance 54, $C_i$, of the buffer amplifier 60, bias resistor 59, $R_{bias}$ and the buffer amplifier 60 with feedback loop 61 and associated output $V_{out}(t)$. DC represents the offset voltage across capacitance 57, $C_e$.

Figure 19:
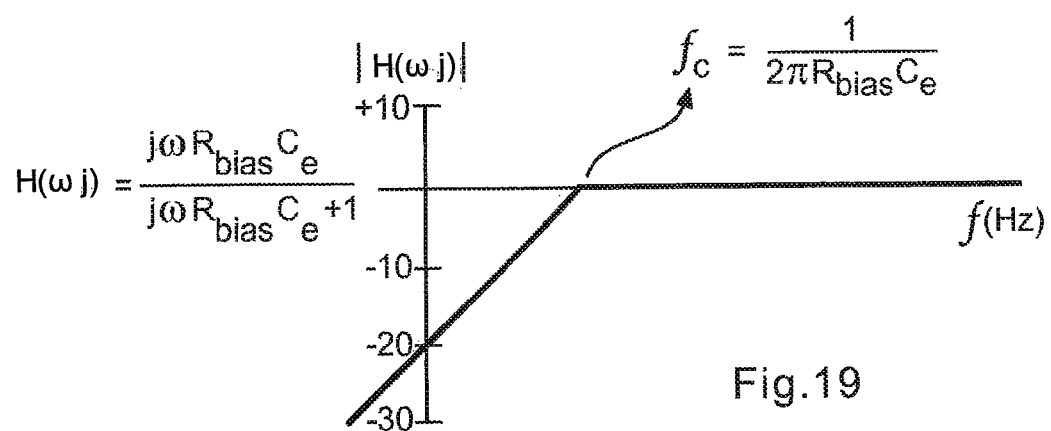

In this embodiment we assume that the input capacitance $C_i$ is eliminated using a known neutralization technique. In FIG. 19 shows the transfer function and the frequency response of the sensor, respectively. In FIG. 19, the transfer function of the capacitive sensor is shown at the left-hand side and the frequency response of the capacitive sensor at the right-hand side.

Figure 20:
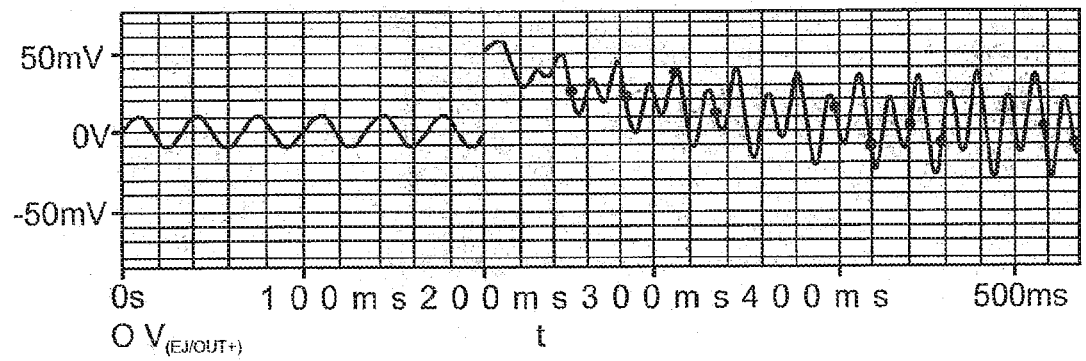

FIG. 20 illustrates the influence of a time-varying skin-electrode coupling in combination with respectively the absence and presence of an offset voltage across the skin-electrode coupling. FIG. 20 illustrates a simulated sensor output voltage with time-varying skin-electrode coupling (60 Hz). From t=0 s to 200 ms a bioelectric signal (10 mV/30 Hz) is measured. From t=200 ms onwards an offset voltage of 50 mV is added, which clearly results in an artifact in the sensor read-out.

Figure 21:
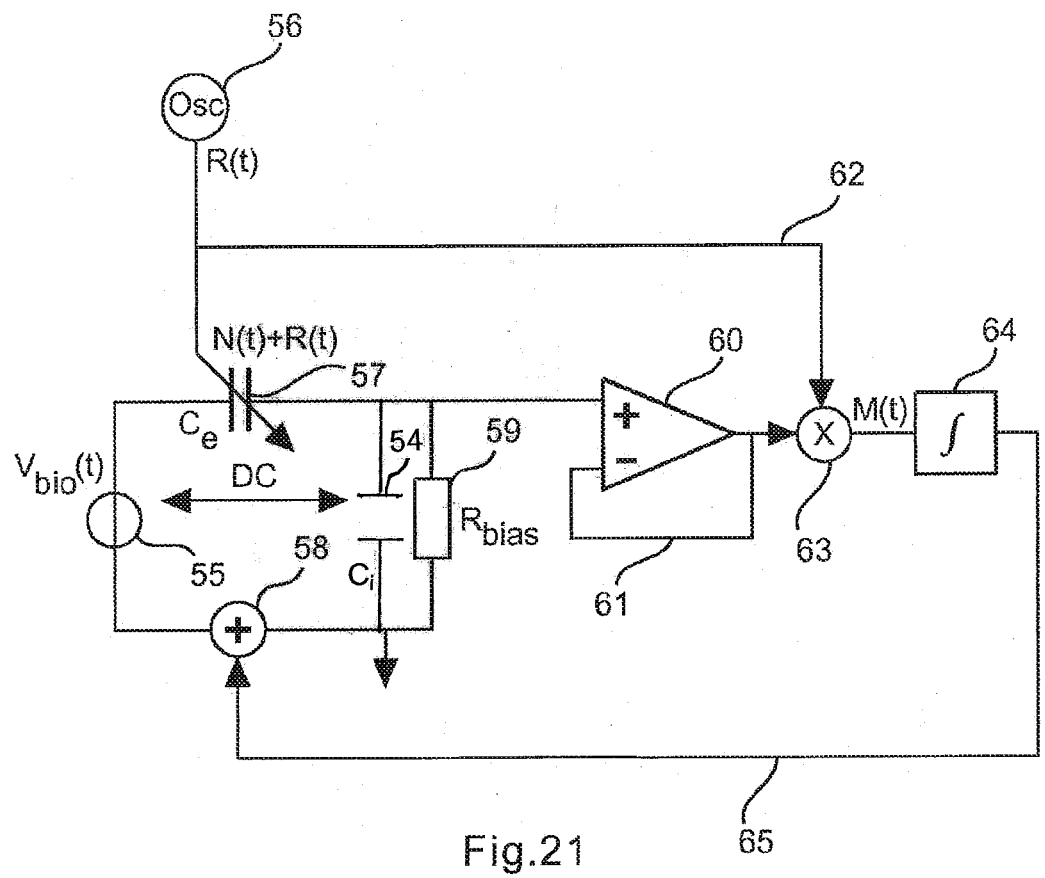
FIG. 21 shows exemplarily another embodiment in accordance with the invention.

In the embodiments according to FIGS. 21 to 24, a method and device are provided that significantly reduce the artifacts by compensating the voltage drop across the skin-electrode capacitance (i.e. electric field) using a vibrating capacitive probe in combination with a synchronous detector and feedback mechanism. This aspect will be explained in more detail by means of FIG. 21. FIG. 21 illustrates an embodiment of a capacitive bioelectric sensor with motion artifact compensation. FIG. 21 shows the bioelectric signal 55, $V_{bio}(t)$, the skin-electrode capacitance 57, $C_e$, which is time-varying according to N(t), the input capacitance 54, $C_i$, of the buffer amplifier 60, the bias resistor 59 $R_{bias}$ and the buffer amplifier 60 with feedback loop 61 and associated output Vout(t). DC represents the offset voltage across capacitor 57, $C_e$.

The motion artifact signal S(t) equals the offset voltage DC times the natural motion signal N(t)

$$S(t)=DC \cdot N(t). \tag{12}$$

By neutralizing the offset voltage, i.e. forcing DC=0, the motion artifacts will be minimized. The method and device described here in order to archive this goal are as follows.

Adding a reference vibration R(t) to the capacitive probe, e.g. a sensor electrode such as electrode 1, 12, results in a motion artifact signal of $$S(t)=DC \cdot (N(t)+R(t)) \tag{13}$$

which is applied to the input of unity gain amplifier 60.

Multiplying, in multiplier 63, equation (18) with the reference vibration R(t) applied via line 62 gives $$M(t) = DC \cdot (N(t) + R(t)) \cdot R(t) \tag{14}$$
$$= DC \cdot N(t) \cdot R(t) + DC \cdot R(t)^2.$$

Preferably R(t) is sinusoid described as R(t)=r cos($\omega_R$t), such that $$M(t)=DC \cdot N(t) \cdot R(t) + \tfrac{1}{2}DC \cdot r^2 \tfrac{1}{2}DC \cdot r^2 \cos(2\omega_R t). \tag{15}$$

The frequency of the vibration $\omega_R$ generated by oscillator 56 is preferably outside the bioelectric frequency band. Integration of equation (20) averages out the AC part of M(t). Next, the output signal of the integrator such as integrator 64, which represents the deviation of DC from zero, is fed back 65 to the body via the reference electrode, e.g. electrode 4 or 11, and effectively subtracted from DC, as shown by adder 58. Alternatively, the output of integrator 64 can be fed back to the sense electrode 1, 12 etc. After convergence of the loop, this results in neutralization of the offset voltage (DC=0) and therefore in a reduction/elimination of the motion artifacts.

Figure 22:
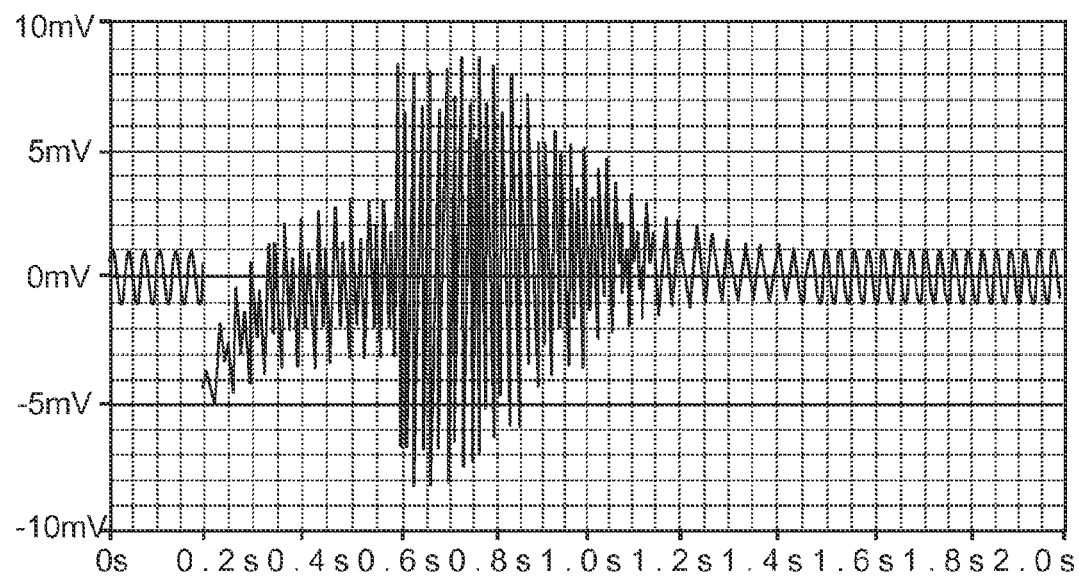
FIG. 22 represents a measurement curve.

According to FIG. 22 a simulation result clearly shows the effect of this motion artifacts reduction technique. According to FIG. 22, from t=0 s to 0.2 s a bioelectric signal (10 mV/30 Hz) is measured. At t=0.2 s a DC voltage (−50 mV) and a natural vibration (60 Hz) is applied, which results in a motion artifact. At t=0.6 s a reference vibration is applied. From t=0.8 s onwards the demodulation and feedback loop is activated, which clearly results in rejection of the motion artifacts: only the bioelectric signal is visible despite the fact that the sensor is experiencing a motion.

Embodiments according to this aspect are not limited to the use of an integrator as described above. Other, more intelligent, filters/controllers are possible, e.g. non-linear controllers or filters with an adaptive bandwidth that combine fast loop convergence and accuracy.

Embodiments according to this and the other aspects of the invention provide a bioelectric signal free from motion artifacts by the use of a vibrating probe.

The statistical independence of the motion-induced signal from the electrophysiological signal can be increased artificially by mechanically mounting the sensor to its housing via an elastic object, such as a spring or cantilever. When excited by an external motion, the resulting mass-spring system oscillates primarily at its natural frequency. As a consequence, a motion-induced signal in the sensor signal will occur in a frequency range that is known a priori, and although the excitation of the vibration may be correlated with the electrophysiological signal, the oscillation is not.

In embodiments, the vibration of the capacitive sensor according to a predefined reference can be performed in different ways.

Figure 23:
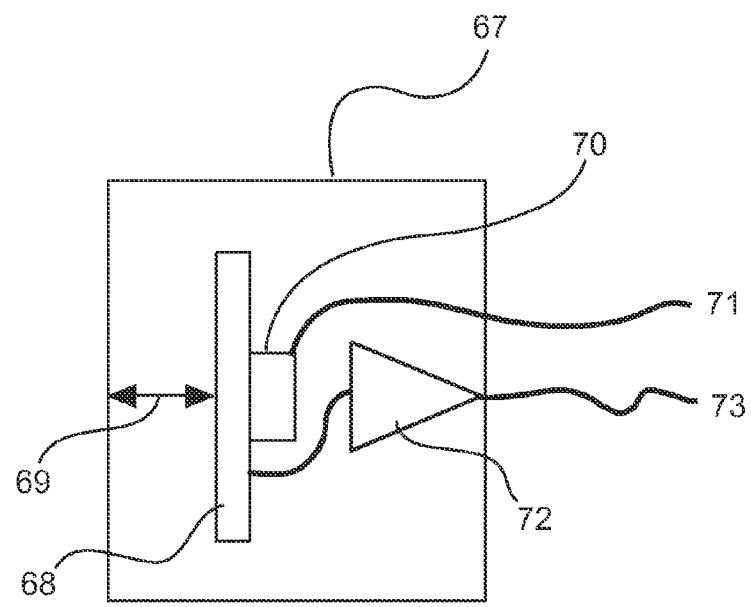
FIGS. 23 and 24 illustrate variations of embodiments in accordance with the invention.
Figure 24:
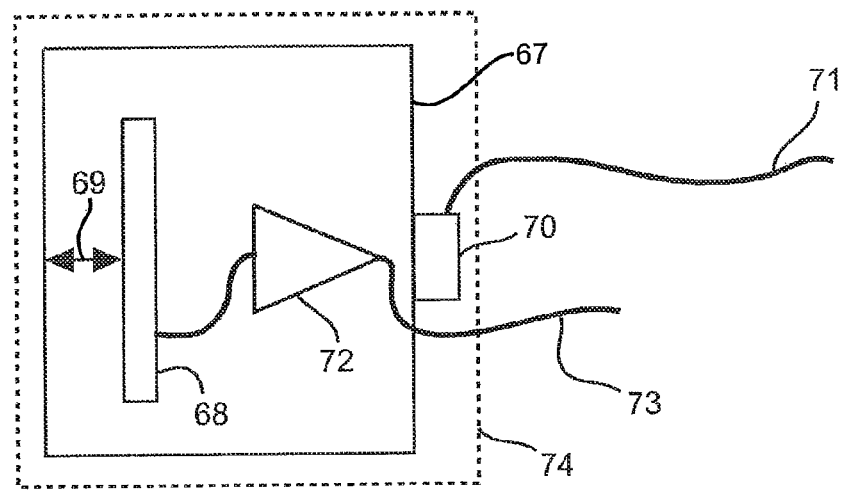

FIGS. 23 and 24 show two possible implementations. Note that this aspect of the invention is not limited to these embodiments.

FIG. 23 shows an implementation of a sensor 67 wherein a vibrating element 70 mounted at the sensor or reference electrode 68 directly mechanically actuates the sensor or reference electrode 68 in the direction of arrow 69. The vibrating element 70 is actuated via an electric line 71. The output signals of the sensor 67 are generated by a buffer amplifier 72 connected to the sensor electrode 68 and output via line 73.

FIG. 24 shows another implementation in which the vibrating element 70 is mounted at the outside or inside of the probe capsule, e.g. the casing of the sensor 67 and directly mechanically actuates the probe capsule, in the direction of arrow 69. The vibrating element 70 is actuated via the electric line 71. The output signals of the sensor 67 are generated by the buffer amplifier 72 connected to the sensor electrode 68 and output via line 73. The sensor 67 is arranged in a housing 74.

In FIGS. 23, 24, both the electrode 68 and buffer amplifier 72 may be properly shielded against external interferences and crosstalk from the vibrating element 70.

The following techniques can for example be used to produce a vibration: electret based motion induction, electromagnetic motion, piezo (including stacked actuator designs and bimorph designs, thermal expansion based motion induction, air pressure and electro-active polymers. In case the vibrating elements cannot produce large desired motion it is possible to use a smart lever system that converts small vibration into large ones. Also operating the vibrating element in resonance can be beneficial, e.g. to reduce energy consumption.

In the following, embodiments will be described which comprise a capacitive sensor with motion artifact reduction using adaptive mixture minimization. These embodiments can be used as individual solutions and can optionally also be combined with parts or all of other embodiments described or shown above or below.

As mentioned above, motion artifacts in capacitive sensors can be reduced by controlling the average electrode-body voltage. The following embodiments propose to extract an indicator of said voltage, directly from the sense electrode signal, and use that indicator to control a compensation signal. The control system can operate at a relatively slow pace, since the average voltage varies only slowly in time, due to e.g. temperature drift and electro-chemical surface changes. The proposed post-processing methods in accordance with one or more of the embodiments exploit the statistical independence of the motion-induced signals and the electrophysiological signal of interest. Since the mixture is partly additive, in an embodiment the indicator used equals the average sensor signal power and the compensation signal is controlled such that the average power is minimized.

As mentioned above, motion induced signals are proportional to both the electric field between electrode and skin and to the motion components along that electric field. Based on this insight it is proposed above to actively control the average voltage between the body and electrode such that the electric field between body and electrode and thus the motion-induced signal are minimized. To control the average voltage between body and electrode, a reference electrode is provided. Since only small and slowly time-varying voltages have to be controlled, the requirements on that galvanic connection are very mild. For example even a reference electrode that touches the body only indirectly through a slightly conductive medium is sufficient. The control can be achieved in various ways, see for some examples the circuit diagrams of FIGS. 2 to 4 showing different configurations for controlling the electrode-body voltage drop, and the further Figures.

In the following embodiments it is proposed to use an indicator of the average voltage between body and electrode that is extracted directly from the sense electrode signal by a post-processing method. Embodiments according to this aspect are based on the insight that the sensor signal may consist of a (partly additive) mixture of electrophysiological signals and motion induced signals. Furthermore, the electrophysiological signal of interest and the motion-induced signals are assumed to be statistically independent, which is reasonable for at least ECG and EEG signals. The indicator provides a means to obtain feedback on the effectiveness of motion artifact reduction and is used to actively control the average voltage.

The statistical independence of the motion-induced signal from the electrophysiological signal can be increased artificially by mechanically mounting the sensor to its housing via an elastic object (see for example FIGS. 21 to 24), such as a spring or cantilever. When excited by an external motion, the resulting mass-spring system oscillates primarily at its natural frequency. As a consequence, a motion-induced signal in the sensor signal will occur in a frequency range that is known a priori, and although the excitation of the vibration may be correlated with the electrophysiological signal, the oscillation is not.

Figure 25:
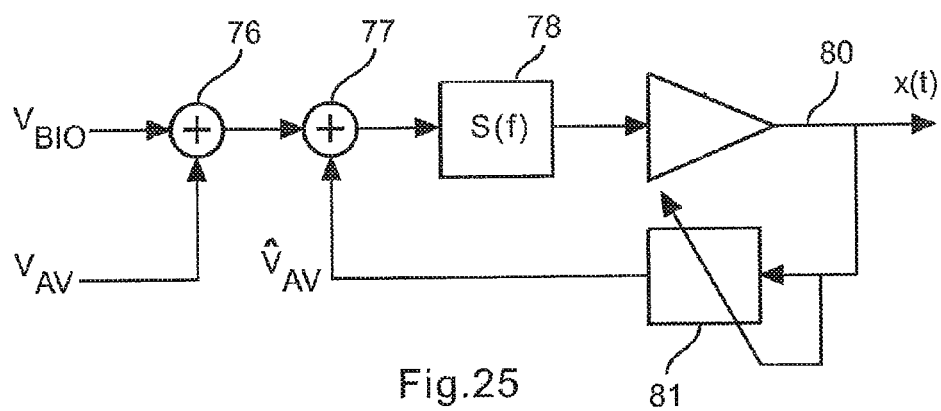
FIG. 25 shows exemplarily a block diagram of another embodiment in accordance with the invention.

The block diagram in FIG. 25 schematically shows a principle of both the problem and embodiments in accordance with the invention. If there exists an average voltage between body and electrode, time-variation of the sensor transfer function 78, S(f), results in motion artifacts of the form S(f) $V_{AV}$. An adaptive post-processing block 81 analyses the sensor output signal 80, x(t,) and produces an output $\hat{V}_{AV}$ such that the electric field between the body and electrode is minimized and the motion-induced signal is reduced. The output $\hat{V}_{AV}$ post-processing block 81 is applied to an adder 77 which further receives the output of an adder 76 adding the sensed signal $V_{BIO}$ to the average voltage $V_{AV}$. Note that the feedback loop comprising the block 81 can be relatively slow because the average voltage between body and electrode varies only slowly due to temperature drift and electro-chemical surface changes. For the optimal average voltage between body and electrode the motion-induced signals are minimized for a wide range of frequencies. Also note that the feedback loop can automatically compensate for various other slowly varying offsets in the system. In the following embodiments, various methods are proposed for sensor signal analysis that retrieve indicators of the average electrode-body voltage by means of digital processing. For that reason, it is assumed that the sensor signal x(t) has been properly sampled and quantized, and that the compensation signal $\hat{V}_{AV}$ can be controlled from the digital domain.

Optionally, motion-induced variations in the transfer of the electrophysiological signal (S(f)$V_{BIO}$) giving rise to a multiplicative motion artifact may be compensated using neutralization to reduce these type of motion artifacts. These techniques can be combined with the below described embodiments in accordance with implementations of the invention.

Figure 26:
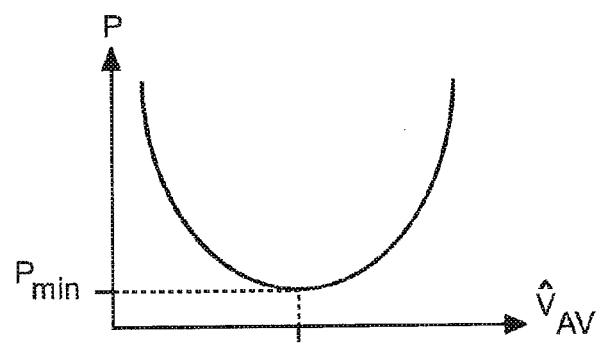
FIG. 26 represents a power curve diagram.

In accordance with one or more of the embodiments an adaptive power minimization is provided. Typically, at least ECG and EEG signals show persistence and regularity over time, and the average signal powers vary only very gradually. The sensor signal consists of an additive mixture of electrophysiological signals and motion induced signals, therefore the average power of the DC-free signal also provides an indication of the average voltage between body and electrode. When the compensation signal $\hat{V}_{AV}$ is varied, a certain value $P_{min}$ exists for which the sensor signal power P and thus the motion-induced signal is minimized, as visualized in FIG. 26, showing the average signal power vs. control signal.

Iterative optimization algorithms, such as gradient descent provide a straightforward method to adapt the compensation signal in order to achieve minimization of the sensor signal power P(t). A typical scheme for updating the compensation signal $\hat{V}_{AV}$ from t=$t_0$ to t=$t_1$, is given by $$\hat{V}_{AV}(t_1) = \hat{V}_{AV}(t_0) - \alpha \frac{\partial P(t)}{\partial \hat{V}_{AV}(t)}\bigg|_{t=t_0} \quad (16)$$

where the adaptation constant α controls the convergence speed and the steady-state noise. The gradient descent method shown here merely serves as an example, since any iterative optimization algorithm can be applied.

A straightforward method to obtain an estimate of the gradient is by finite difference approximation, i.e.

$$\frac{\partial P(t)}{\partial \hat{V}_{AV}(t)}\bigg|_{t=t_1} = \frac{P(t_1) - P(t_0)}{\hat{V}_{AV}(t_1) - \hat{V}_{AV}(t_0)} \quad (17)$$

where it is assumed that the compensation signal values at $t_0$ and $t_1$ are not equal. Other methods based on modulation or wobbling can also be applied to determine the local gradient.

In the above embodiments, the average power of the sensor signal is used as the minimization criterion. Alternatively, the sensor signal can be pre-filtered, such that only a certain frequency band is used for which the power is determined. Depending on the practical application, this alternative approach can provide better separation of electrophysiological signals and motion-induced signals and increase the robustness of the method.

In accordance with one or more other embodiments, an adaptive Shannon entropy minimization is used. The Shannon entropy quantifies the average information content in a signal. The sensor signal consists of an additive mixture of electrophysiological signals and motion induced signals, and entropy minimization by adapting $\hat{V}_{AV}$ provides a means to reduce motion artifacts. The information entropy is determined by the probability mass function p(x) of the signal, i.e.

$$H(X) = -E\{\log x\} = -\sum_{x \in X} p(x)\log p(x) \quad (18)$$

where the base of the logarithm, e.g. e, 2, or 10, determines the entropy unit, which is simply a gain factor in the feedback. In practice, the data is discrete and H (X) typically is obtained from a probability mass function estimate p̂(x), e.g. the histogram, therefore $$\hat{H}(X) = -\sum_{i=1}^{n} \hat{p}(x_i) \log \hat{p}(x_i). \quad (19)$$

The lower the entropy, the more predictable is the signal, and the less information is contained. Again, iterative optimization can be applied, e.g. steepest descent, to update the compensation signal and the gradient can be obtained by e.g. finite difference approximation, so $$\hat{V}_{AV}(t_1) = \hat{V}_{AV}(t_0) - \alpha \frac{\partial \hat{H}(X, t)}{\partial \hat{V}_{AV}(t)}\bigg|_{t=t_0}. \quad (20)$$

Note that algorithms based on other information-theoretic measures, such as negentropy, non-Gaussianity, etc. can also be used as an indicator of the independent components in the signal.

In the following, embodiments will be described which can be used alone or in arbitrary combination with other embodiments as described or shown above or below.

An adaptive probe transfer equalization for capacitive sensing of biosignals is proposed.

As mentioned above, motion-induced artifacts are induced where the coupling capacitance is changing due to skin-electrode distance variation induced by movements of the test subject, causing deterioration of the measured electrophysiological signal. This problem becomes larger in applications where the measurements are performed on free-moving subjects.

Figure 27:
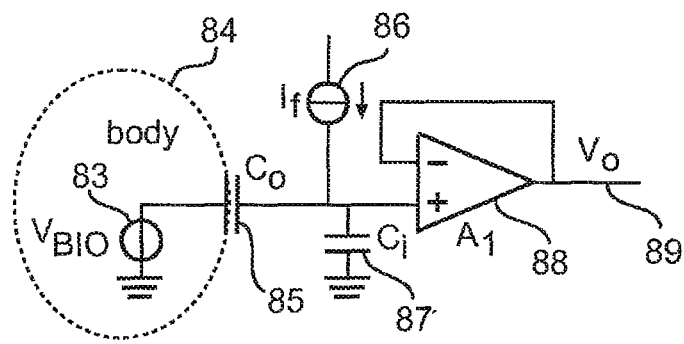
FIGS. 27 to 30 illustrate further embodiments in accordance with the invention.

FIG. 27 depicts an electrical model of a typical probe 83 connected to a human body 84 and providing capacitive sensing and buffering. A buffer 88 ($A_1$) is connected to a measurement capacitor 85 $C_e$ in order to convert the impedance level from high-ohmic to low-ohmic, such that it can be transported across a cable 89 to the measurement system without being affected by interference. This buffer 88 has an a priori unknown input capacitance 87. The buffer input capacitance 87 can however be of the same order of magnitude as the measurement capacitance $C_e$. Therefore, as a result of capacitive division the output signal $V_o$ of the buffer 88 is given by $$V_0 = \frac{C_e}{C_i + C_e} V_{bio} \quad (21)$$

where $V_{bio}$ is the electrophysiological signal of interest. It can be seen that variations in $C_e$ as a result of motion cause variations in the transfer $V_o/V_{bio}$, which degrade the measurement. A transfer that is independent of $C_e$ can be obtained by actively "shielding" $C_i$ i.e. making $C_i$ virtually zero, resulting in a transfer $V_o/V_{bio}$ equal to one. This can be done as shown in the embodiment of FIG. 28.

The embodiment of FIG. 27 implements "shielding" of capacitor 87 $C_i$ by applying feedback current $I_f$ 86. By feeding back an amount of current $I_f$ to the buffer input node equal to that flowing through $C_i$, $C_i$ is made virtually zero as seen from $C_e$. I.e. no part of the current flowing through $C_i$ is supplied by $C_e$, such that, since there is no current flowing through $C_e$, no voltage drops appear across $C_e$. Therefore the transfer $V_o/V_{bio}$ effectively equals one.

Figure 28:
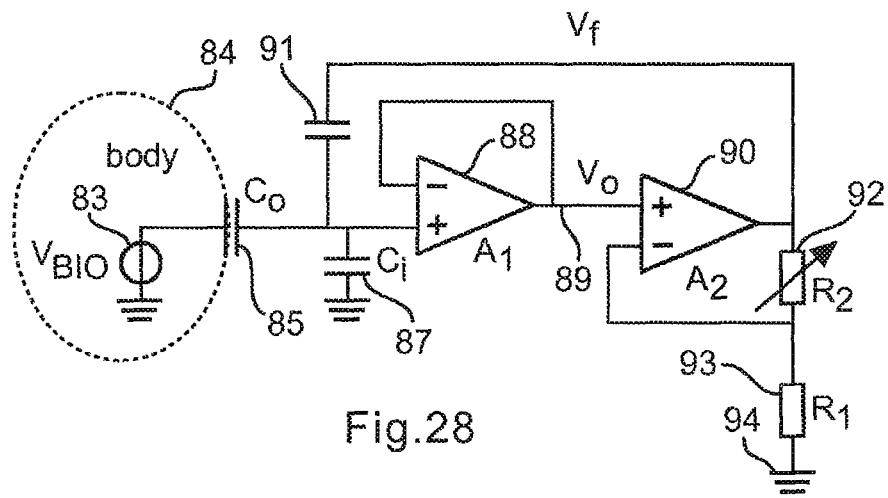

Feeding back the correct amount of current $I_f$ can be achieved using the circuit in FIG. 28, illustrating a method to control the feedback current to shield $C_i$. Here the output $V_o$ of the buffer 88 is amplified using a non-inverting amplifier 90, $A_2$, and subsequently fed back to the input of the buffer 88 via a feedback capacitor 91, $C_f$.

The required output voltage $V_f$ of buffer 90 $A_2$ can be determined from the values of the capacitors 87, 91 and the notion that the gain of the buffer equals one, such that the voltage on the positive input of the buffer 88 equals $V_o$. Hence $$V_o = \frac{C_f}{C_i + C_f} V_f. \quad (22)$$

Furthermore, the output signal of buffer 90, $A_2$, is applied to a controllable series resistor divider 92 (R2), 93 (R1) connected in series between the output of buffer 90 and ground or reference potential 94. The output signal of buffer 90 is given by $$V_f = \frac{R_1 + R_2}{R_1} V_o. \quad (23)$$

Hence, assuming fixed $R_1$, potentiometer $R_2$ should be adjusted such that $$R_2 = R_1 \frac{C_i + C_f}{C_f} - R_1. \quad (24)$$

This solution provides buffer input capacitance compensation.

Usually, a priori $C_i$ is unknown. With the solution described below, it is not necessary to adjust the potentiometer 92 for each probe manufactured, which is a time-consuming and therefore expensive process. Moreover, $C_i$ may vary during operation of the probe, for instance as a function of temperature, causing the transfer function $V_o/V_{bio}$ to deviate from one. The measurement is independent of the probe capacitance ($C_e$) if and only if the current flowing through the buffer input capacitance ($C_i$) is compensated exactly. The solution avoids reduction of the robustness and accuracy of the measurement which might otherwise be caused when the transfer $V_o/V_{bio}$ deviates from unity and as a consequence the sensitivity to motion artifacts increases. For this reason, it is an object of these embodiments of the invention to automatically and adaptively control the transfer $V_o/V_{bio}$, such that equalization is achieved even though the characteristics of the electronics drift.

Figure 29:
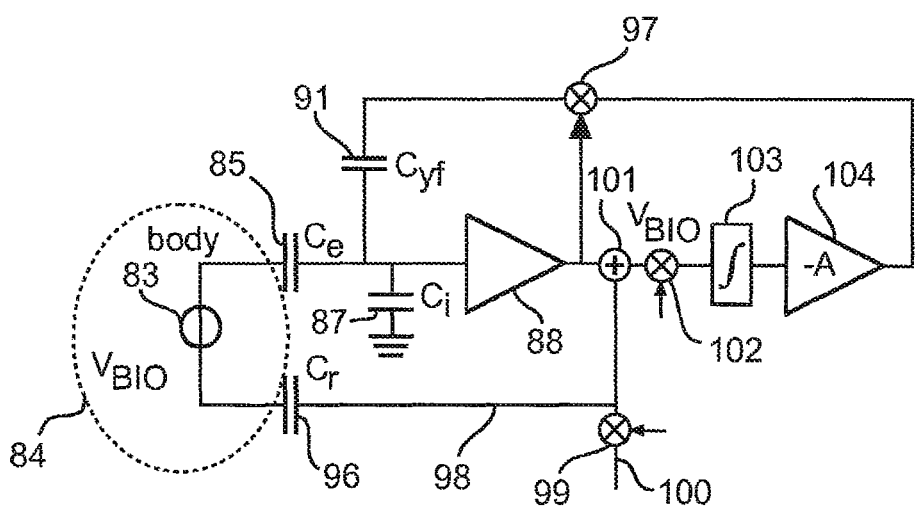

FIG. 29 illustrates an embodiment in accordance with the invention and depicts a block schematic representation of the feedback control loop employed to equalize the transfer $V_o/V_{bio}$. In the embodiments of FIG. 29 the feedback control loop is adapted to adaptively control the transfer of the buffer stage. The description of reference numerals used in FIGS. 27, 28 likewise applies to similar reference numerals of FIG. 29. The method and device make use of a reference signal $V_{ref}$ on line 98, that is applied to the body 84 via a capacitor 96, $C_r$. Optionally, the capacity value of capacitor 96, $C_r$ is much larger than that of capacitor 85, $C_e$, for example by a magnitude of, or more than five, optionally of, or more than ten or fifty, such that the transfer of the reference signal through the body to the buffer output is essentially equal to the transfer of the biosignal to the buffer output. In a practical application this condition is easily met, since the probe electrodes, e.g. 1 of FIGS. 2 to 5, are typically restricted in size to allow for localized biosignal measurement, whereas the reference electrode plate, e.g. 4, can have arbitrary size. The reference signal should not interfere with the biosignal measurement; therefore a reference 100 defining the setpoint (which may have an arbitrary value) is modulated, by multiplier 99, well above the maximum frequency that is expected in the signal of interest, which may for example be several hundred Hz. Under these two conditions, equalization of the reference signal transfer results in equalization of the biosignal transfer. Note that the application of the reference signal is provided for the purpose of equalizing the buffer input capacitance of capacitive biosignal sensing.

Equalization may be achieved using the shown feedback control loop. The reference signal is picked up by the capacitive sensor 96 and amplified with a factor that is ideally one, but initially lower than that. The applied reference signal is then subtracted, via subtracter 101 from the measured and buffered reference signal, such that, if the total amplification is smaller than one, the result of this subtraction still contains some of the reference signal. This signal is demodulated, by multiplier 102 using the same frequency as that applied to the multiplier 99, and low pass filtered, such that we obtain a DC signal indicative of the deviation of the amplification from one. This signal is finally used to control the amplification. For that purpose the obtained DC signal is applied to an integrator 103, amplified by amplifier 104 and subsequently used by multiplier 97 to control the amount of signal that is fed back from the output of buffer amplifier 88 via a feedback capacitor 91 ($C_f$) in order to set the amplification equal to unity. The employment of an integrator 103 means that the control loop will continue to change the feedback current until the steady state error is zero, i.e. the signal at the output of the buffer amplifier 88 is equal to the reference signal applied. In other words, its gain is equal to one. The signal of interest, i.e. $V_{bio}$ is now present at the output of the subtracter 101. Note that the modulation signal is not restricted to a sinusoidal, as is shown in FIG. 29, but can be an arbitrary waveform, as long as the spectral distribution is well separated from the spectrum of the signal of interest.

Figure 30:
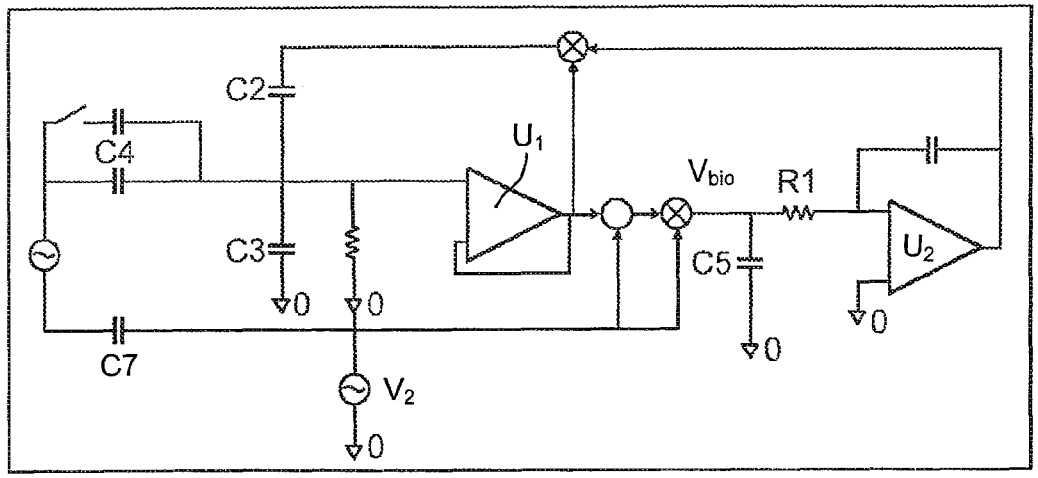

FIG. 30 depicts a practical circuit representing the block scheme of FIG. 29, which was used during simulation. Here the reference voltage $V_2$ is applied to the body via $C_7$ where it is added to the signal of interest $V_{bio}$. The total signal is transferred via the capacitive sensor, represented by $C_4$, to the buffer $U_1$. The reference signal is then subtracted from the buffered signal, and the result demodulated to DC by multiplication by the reference signal. The demodulated signal is then low-pass filtered and integrated $R_1$, $C_5$. The output of the inverting integrator ($U_2$) represents the factor by which the buffer output signal should be amplified before being fed back to its input via the feedback capacitor $C_2$, in order to shield the buffer input capacitance $C_3$.

Note that the modulation and demodulation can be implemented as a multiplier, as is shown in FIG. 30, but can also be implemented using switches.

Note that a so-called bleeder can provide a path to ground for any op-amp bias current. The resistance does not influence the working of the circuit and can be omitted in a practical implementation.

Figure 31:
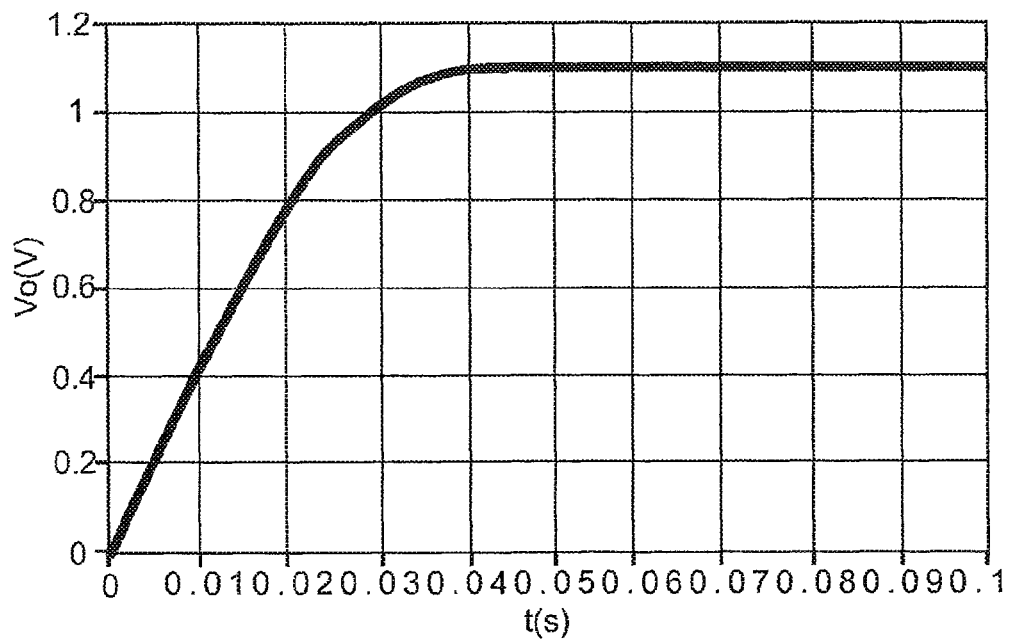
FIGS. 31 and 32 represent voltage ratio-time diagrams.
Figure 32:
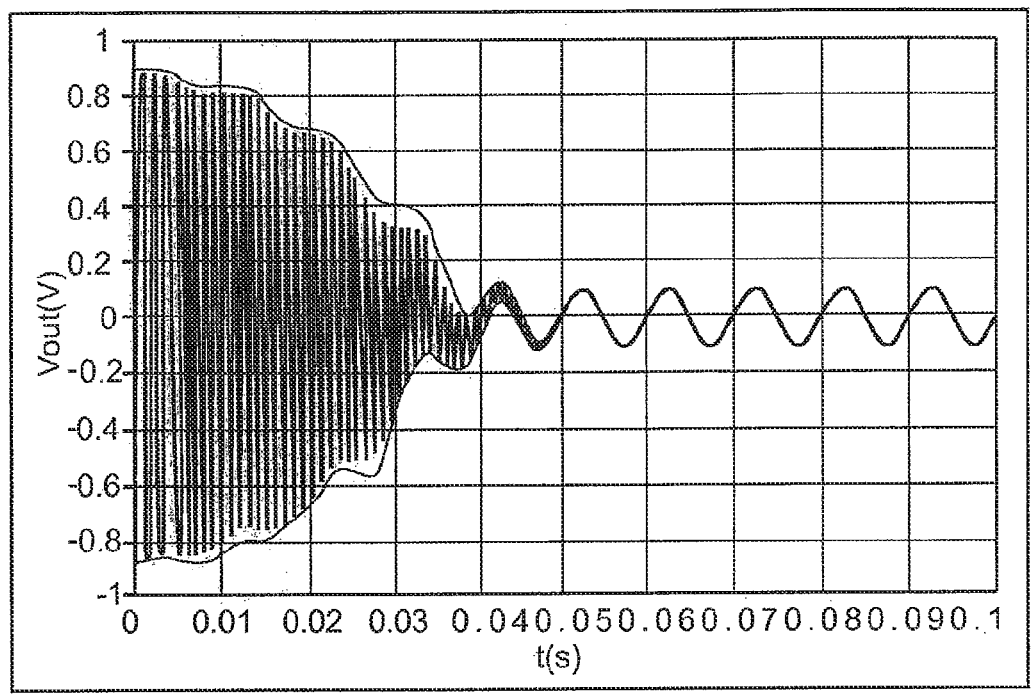

In the simulation a reference signal of amplitude 1 V and frequency 10 kHz was used. The bio signal was chosen to have amplitude of 0.1 V and a frequency of 100 Hz. FIG. 31 depicts the output signal of the integrator (corresponding to 103 in FIG. 29), which clearly converges within 50 ms to a steady state value. FIG. 32 depicts the output signal of the subtraction (corresponding to 101 in FIG. 29), which should after convergence, i.e. after the correct compensation current is fed back, be equal to the applied $V_{bio}$. It can be seen that indeed at first there is a large reference signal component presents in the signal, which reduces to zero upon convergence, such that only the signal $V_{bio}$ remains.

A change in $C_e$ was furthermore simulated by closing switch $U_3$ at t=0.05 s, such that at that time $C_e$ changes from 10 pF to 20 pF. It can be seen from FIG. 32 illustrating the signal at output of subtraction, i.e. the signal of interest, that the signal of interest is not affected by the change in $C_e$.

Evidently, the bandwidth and the gain determine the convergence and tracking speed, but also the accuracy equalization. Specific settings can be tuned to the probe design and application requirements.

Figure 33:
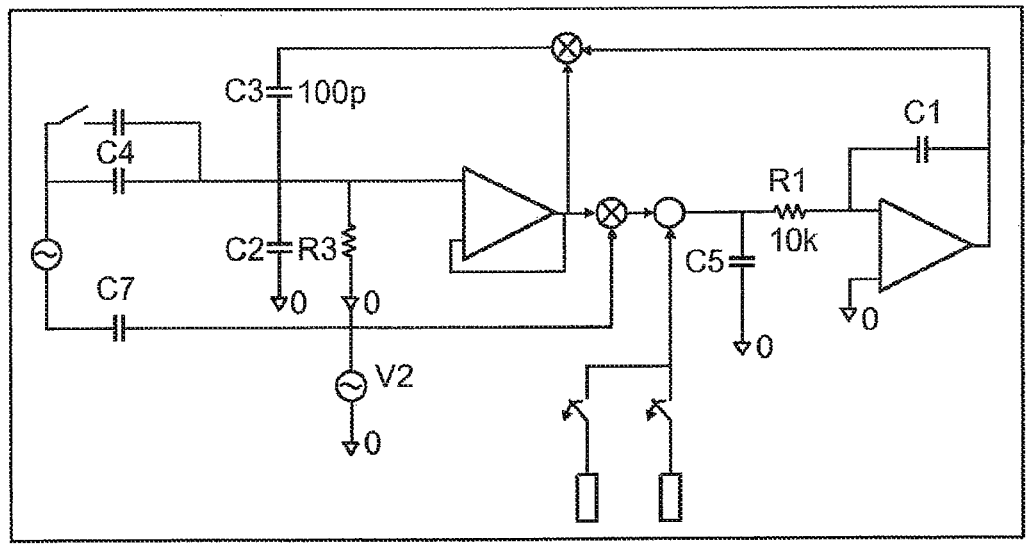
FIGS. 33 and 34 show circuit configurations in accordance with embodiments of the invention.

In a further embodiment, which is shown in FIG. 33, the subtraction of the reference signal is performed after demodulation, such that a constant value can be subtracted. Note that for a reference signal with an amplitude of 1 V the value to be subtracted is equal to 0.5 V, since the demodulation gives rise to an attenuation of a factor 2. The signal of interest now appears at the output of the buffer, but is optionally in this embodiment still be low-pass filtered to remove the reference component at 10 kHz.

Figure 34:
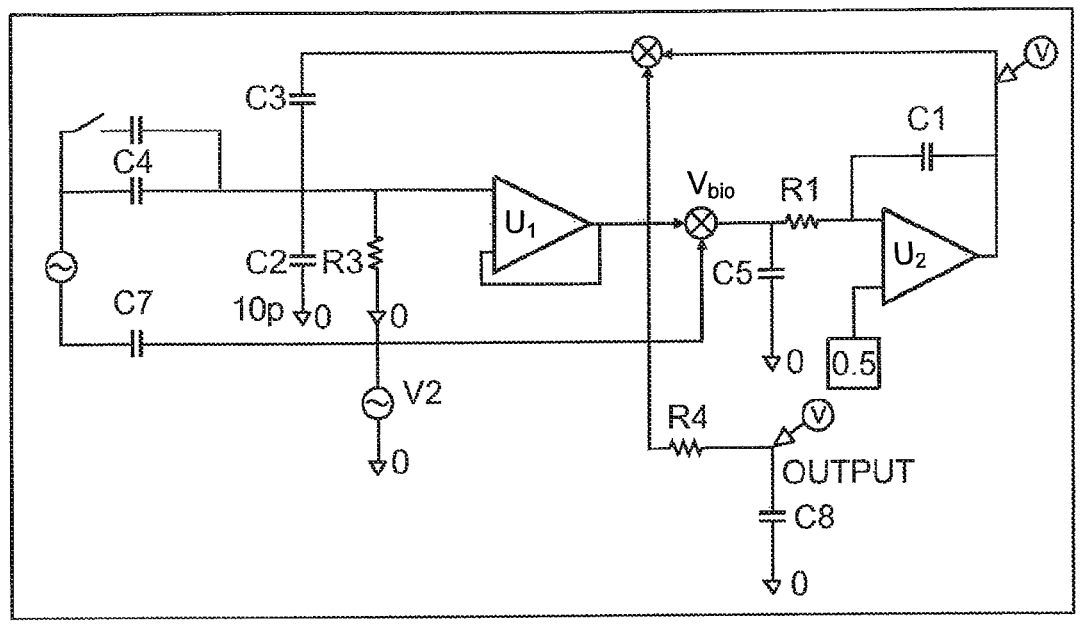

In another embodiment, shown in FIG. 34, the subtraction is performed by applying the constant value of 0.5 V to the positive input of the integrator $R_1$, $C_5$, $U_2$. This embodiment has the advantage that a discrete subtraction is not required. In FIG. 34, a low-pass filter R4, C8 is furthermore employed to filter the output signal of the buffer $U_1$ in order to obtain the signal of interest $V_{bio}$.

Figure 35:
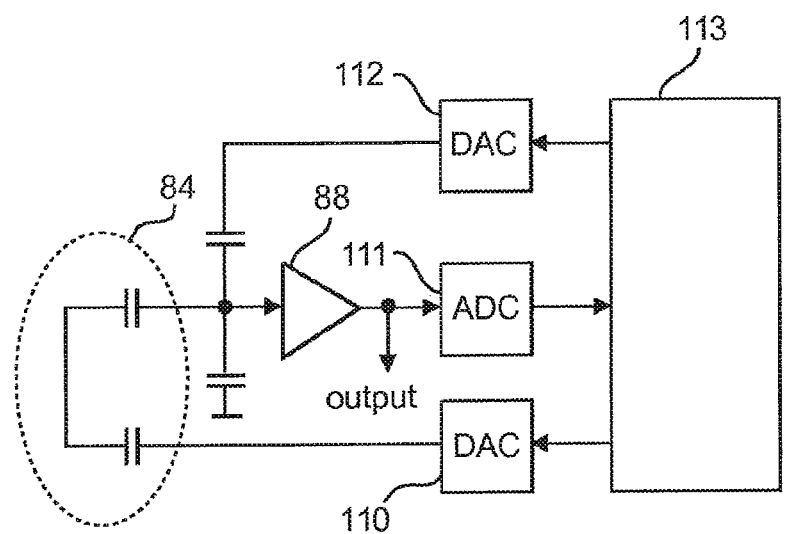
FIG. 35 illustrates a digital design in accordance with one or more embodiments of the invention.

In a further embodiment, the equalization scheme is implemented in the digital domain, as visualized in FIG. 35 showing a digital implementation of the equalization method. Like reference numerals in this and/or other drawings designate like components. The reference signal is created by a digital control system 113 and applied to the body 84 by a digital to analog converter (DAC) 110. The output signal of the buffer 88 is digitized by an analog to digital convertor (ADC) 111 and routed to the control unit 113. Demodulation, filtering and integrating is then done in the digital domain of 113. The feedback signal is deduced from the buffer output signal and applied to the buffer input via a DAC 112 or alternatively via a multiplying DAC.

In some embodiments described above, it is proposed to actively control the average voltage between the body and electrode such that the electric field between body and electrode and thus the motion-induced signal are minimized. Further, it is proposed to extract an indicator of such voltage, directly from the sensed electrode signal, and use that indicator to control a compensation signal. The proposed post-processing methods exploit the statistical independence of the motion-induced signals and the electrophysiological signal of interest. Since the mixture is partly additive, the indicator used may optionally equal the average sensor signal power and the compensation signal is controlled such that the average power is minimized.

In the embodiments described below, it is proposed to actively control the average voltage between the body and electrode to minimize the motion-induced signal. Another manner of deriving the compensation signal is provided. In these embodiments it is proposed to reconstruct the input signal using the measured variation of the capacitance of the electrode and derive the compensation signal from further processing the reconstructed signal. Furthermore, since the variation of the electrode capacitance is known, the modulating effect of the time-varying capacitance on the electrophysiological signal can be removed. The parameters of the capacitive sensing circuit, such as the load (R), the stray capacitance ($C_i$) are known or can be estimated.

Figure 36:
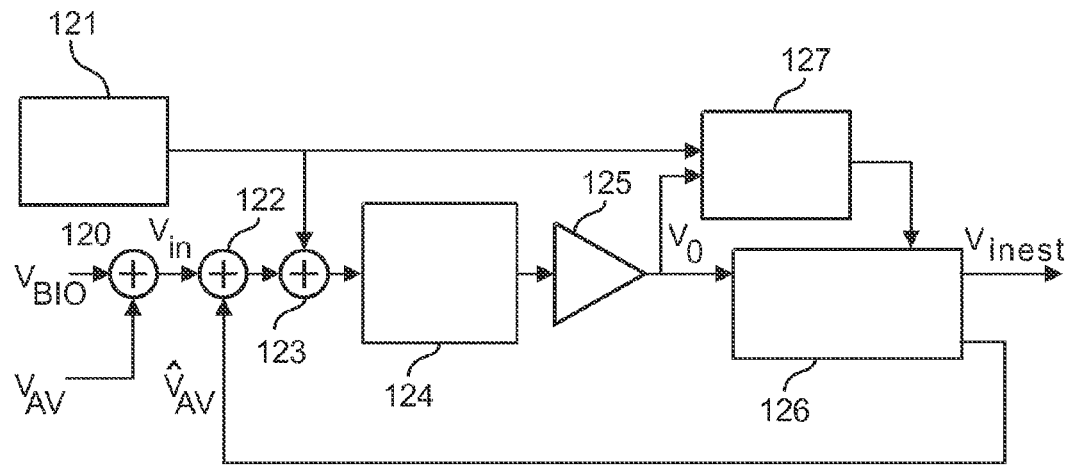
FIG. 36 shows a block diagram in accordance with an embodiment of the invention.

In the embodiment of FIG. 36, an adder 120 is provided for adding the biosignal $V_{BIO}$ and the signal $V_{AV}$. The output signal $V_{IN}$ of the adder 120 is supplied to a further adder 122 which receives at its other input a feedback signal $\hat{V}_{AV}$, and supplies its output signal to a further adder 123. The other input of adder 123 receives a signal generated by signal generator 121. The output of adder 123 is connected to block 124 providing a time varying capacitive coupling. A buffer amplifier 125 is connected to the output of block 124 and generates an output signal $V_o$ which is supplied to the input of an estimate circuit 127 for estimating $C_e(t)$ as well as to the input of a circuit 126 configured to derive $V_{in}$ and the compensation signal which is fed back to the input of adder 122.

Figure 37:
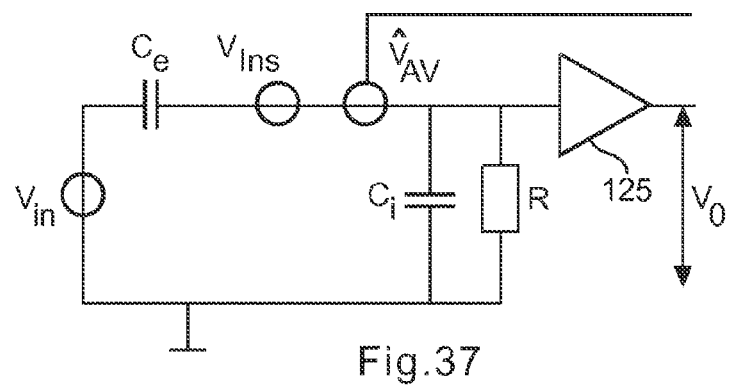
FIGS. 37 and 38 show circuit configurations in accordance with embodiments of the invention.
Figure 38:
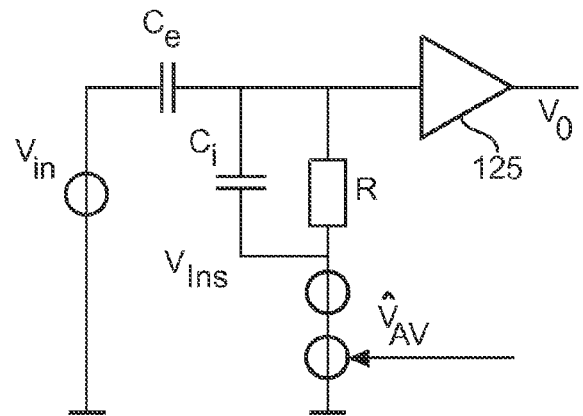

FIGS. 37 and 38 show two equivalent circuit diagrams of FIG. 36. These circuit diagrams are used to illustrate this embodiment of the invention.

The variation of the electrode capacitance ($C_e(t)$) can be measured, for instance, by using a known signal injection technique. The inserted voltage $V_{Ins}$ may be a carrier wave at a frequency $F_c$ much larger than the frequencies of interest in the input signal. At the output, this carrier is modulated by a time-dependent factor $C_e(t)/(C_i+C_e(t))$, which allows for the reconstruction of $C_e(t)$. This method to estimate the time-varying capacitance ($C_e(t)$) may also be replaced by another suitable method.

In the following a method to derive $V_{in}$ and compensation signal will be described, as implemented in block 126.

The output signal $V_o$ in FIGS. 37, 38 generated by buffer 125 is related to the input signal $V_{in}$ as follows:

$$V_o(t) = \frac{C_e(t)}{C_e(t)+C_i}V_{in}(t) - \frac{1}{C_e(t)+C_i}\int_0^t \frac{V_o(s)}{R}ds - \frac{1}{C_e(t)+C_i}Q_{init}. \quad (25)$$

Equation (1) can be rewritten as follows $$V_{in}(t) = \left(1 + \frac{C_i}{C_e(t)}\right)V_{in}(t) + \frac{1}{C_e(t)}\int_0^t \frac{V_o(s)}{R}ds - \frac{1}{C_e(t)}Q_{init}. \quad (26)$$

Hence $V_{in}$ can be reconstructed if $V_o(t)$, $C_e(t)$, R, $C_i$, and $Q_{init}$ are known.

$Q_{init}$ may be estimated, for instance, by assuming that the correlation between the time-varying part of $1/C_e(t)$ and $V_{in}(t)$, equals zero, i.e., $$\int_0^T V_{in}(t-\tau)\left(\frac{1}{C_e(t-\tau)} - \left[\frac{1}{C_e}\right]_{av}\right)d\tau = 0 \quad (27)$$

for a suitable value of T. This yields a linear equation in $Q_{init}$.

This procedure is equivalent to choosing $Q_{init}$ such that the signal power $$\int_0^T V_{in}(t-\tau)^2 d\tau$$

is minimized.

The compensation signal is then derived from the average of the reconstructed $V_{in}$.

Note that the DC-offset can be of the order of volts, whereas the biosignal to be measured is typically of the order of millivolts. This means that a small relative error in the above calculation of $Q_{init}$ would still give a large relative error in the reconstructed signal. This is the reason why active compensation, i.e., reducing the DC-offset by the compensation signal, is provided.

Applications of embodiments of the invention include any application in which electrophysiological fields (ECG, EMG, EEG, EOG, EHG, . . . ) are probed or sensed. Any one of such applications are potential candidates where capacitive sensors such as the sensors disclosed in the present specification and drawings can be applied. Some examples where capacitive sensors can be used are patient monitors (mostly ECG), EEG probing device (clinical), brain computer interface (BCI), pregnancy belts containing sensors for monitoring baby condition or uterine activity, EMG probing device to monitor muscle use in order to prevent muscle overload or RSI, device that monitors ECG or EMG during physical activity/sports or devices that interpret emotions based on electrophysiological signals. Since capacitive sensors have the unique capability to measure through insulating materials new possibilities arise like measuring through bandages, e.g. in case of burn wounds or measure electrophysiological signals in a 'smart bed'.

Embodiments may for example be applied in the patient monitoring sector, optionally with capacitive sensors having sufficient robustness. Further, embodiments may be used in the field of home monitoring in which user friendly probing of body vital signs (e.g. the ECG) is beneficial.

Embodiments in accordance with the invention may be applied for medical and healthcare devices, CE products and other applications where electrophysiological signal (e.g., ECG, EMG, EEG and etc.) measurements, especially by means of contactless (capacitive coupling), are performed. As an example embodiments may be used for smart beds providing a platform for measurements e.g. during the night.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Features recited in separate embodiments or dependent claims may be advantageously combined in any arbitrary combination.

While the invention has been illustrated and described in detail in the drawings and foregoing description, such illustration and description are to be considered illustrative or exemplary and not restrictive; the invention is not limited to disclosed embodiments. For example, it is possible to operate the invention in an embodiment for measuring other signals such as non-biological signals.

Any reference signs in the claims should not be construed as limiting the scope.

Calculations, processes, steps, and determinations performed by one or several units or devices can be performed by any other number of units or devices. For example, the method steps can be performed by a single unit of by any other number of different units. The calculations and determinations and/or the control of the system and/or of the device in accordance with the above described methods can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. An apparatus configured to measure at least one electrophysiological signal of a body, comprising:
    at least one capacitive sensor electrode;
    a vibrator configured to vibrate the at least one capacitive sensor electrode, or a support or casing supporting or housing the at least one capacitive sensor electrode, and
    a feedback loop coupled to the vibrator to generate a feedback signal to control an average voltage between the at least one capacitive sensor electrode and the body for reducing or minimizing the average voltage.

2. The apparatus according to claim 1, wherein the frequency of the vibration is outside of a bioelectric frequency band of the electrophysiological signal to be measured.

3. An apparatus configured to measure at least one electrophysiological signal of a body, comprising:
    at least one capacitive sensor electrode which generates a sensor output signal which includes an additive mixture of the at least one electrophysiological signal and motion induced signals;
    a circuit configured to control an average voltage between the at least one capacitive sensor electrode and the body, the circuit including:
        a processing circuit configured to estimate a power or an entropy of the sensor output signal of the at least one capacitive sensor electrode,
        a feedback subcircuit configured to generate a feedback signal based on the average voltage, and
        a control subcircuit configured to bring the average voltage to a defined value;
    wherein the processing circuit is configured to estimate the average voltage and iteratively adjust the estimated average voltage based on a slope of a change in the estimated power or entropy relative to a change in the average voltage and wherein a convergence speed to the estimated average voltage is slower than an oscillation rate of the electrophysiological signal.

4. An apparatus configured to measure at least one electrophysiological signal $V_{bio}$ of a body comprising:
    at least one capacitive sensor electrode which has a measurement capacitance and outputs a measurement signal including the at least one electrophysiological signal $V_{bio}$ and a motion component;
    a reference electrode configured to output a reference signal $V_{ref}$;
    a buffer amplifier configured to receive the at least one electrophysiological signal $V_{bio}$ and output an output voltage $V_o$;
    a subtraction circuit configured to subtractively combine the output voltage $V_o$ and the reference signal $V_{ref}$;
    an integrator configured to integrate the subtractively combined output voltage $V_o$ and the reference signal $V_{ref}$ and derive an equalizing feedback signal $V_f$;
    a capacitive network connected between the at least one capacitive sensor and the buffer amplifier; and
    an equalizing circuit configured to feedback the equalizing feedback signal $V_f$ to the capacitive network for equalizing a transfer function $V_o/V_{bio}$ to adaptively control the transfer function $V_o/V_{bio}$, such that the equalizing feedback signal $V_f$ brings a gain of the buffer amplifier to unity.

5. The apparatus according to claim 4, further comprising:
    means configured for modulating the reference signal $V_{ref}$ to a value above a maximum expected frequency of the electrophysiological signal of interest, and
    means configured for demodulating the subtractively combined output voltage $V_o$ and reference signal $V_{ref}$ to generate a demodulated subtractively combined output voltage $V_o$ and reference signal $V_{ref}$ for integration by the integrator to generate the equalizing feedback signal $V_f$.

6. An apparatus configured to measure at least one electrophysiological signal of a body, comprising:
    at least one capacitive sensor electrode;
    at least one reference electrode arranged to be close to or in galvanic contact with the body, wherein the at least one reference electrode is connected to a voltage source, a current source or a reference potential; and
    a circuit configured to actively control an average voltage between the at least one capacitive sensor electrode and the body by reducing or minimizing an electric field between the at least one capacitive sensor electrode and the body to reduce or minimize motion-induced signals caused by the electric field and variations in a distance between the at least one capacitive sensor electrode and the body, wherein the circuit includes:
        an oscillator configured to generate an oscillating signal with a higher frequency than a frequency of the electrophysiological signal;
        a modulator configured to modulate one of a signal from the capacitive sensor or a reference signal indicative of motion induced components with the oscillating signal;
        an amplifier configured to amplify the electrophysiological signal;
        a demodulator configured to demodulate the amplified electrophysiological signal with the oscillating signal; and
        an integrator configured to integrate the demodulated amplified electrophysiological signal to generate a feedback signal to control the average voltage.

7. The apparatus according to claim 6, wherein the at least one sensor electrode includes at least two sensor electrodes coupled to inputs of a differential amplifier.

8. The apparatus according to claim 6, wherein the at least one sensor electrode includes at least two sensor electrodes configured to measure essentially the same electrophysiological signal and adapted to be arranged at different distances to the body and/or supplied with different average voltages, a feedback signal being generated based on output signals of the sensor electrodes so as to bring the average voltage to a defined value.

9. The apparatus according to claim 8, wherein the at least one sensor electrode includes at least three sensor electrodes, the at least three sensor electrodes being arranged:
- in a triangular fashion, or
- in concentric circles, or
- in the form of small segments, the segments of all electrodes being distributed in an interspersed manner, or
- in segments arranged as a ring or a matrix.

10. The apparatus according to claim 6, further including at least one buffer amplifier configured to convert an output signal of the at least one capacitive sensor electrode, applied to an input of the buffer amplifier, into an output signal while keeping the average voltage on the at least one capacitive sensor electrode at a level defined by a signal applied to a further input of the buffer amplifier.

* * * * *